(12) United States Patent
Sjölund

(10) Patent No.: US 11,367,520 B2
(45) Date of Patent: Jun. 21, 2022

(54) COMPRESSING RADIOTHERAPY TREATMENT PLAN OPTIMIZATION PROBLEMS

(71) Applicant: Elekta AB (publ), Stockholm (SE)

(72) Inventor: Jens Olof Sjölund, Stockholm (SE)

(73) Assignee: Elekta AB (publ), Stockholm (SE)

( * ) Notice: Subject to any disclaimer, the term of this patent is extended or adjusted under 35 U.S.C. 154(b) by 166 days.

(21) Appl. No.: 16/512,962

(22) Filed: Jul. 16, 2019

(65) Prior Publication Data

US 2021/0020296 A1 Jan. 21, 2021

(51) Int. Cl.
*G16H 50/20* (2018.01)
*G16H 20/40* (2018.01)

(52) U.S. Cl.
CPC ............ *G16H 20/40* (2018.01); *G16H 50/20* (2018.01)

(58) Field of Classification Search
CPC ....... G16H 20/40; G16H 50/20; A61N 5/1031
See application file for complete search history.

(56) References Cited

U.S. PATENT DOCUMENTS

| 2004/0165696 | A1 | 8/2004 | Lee | |
|---|---|---|---|---|
| 2006/0256915 | A1 | 11/2006 | Otto et al. | |
| 2017/0177812 | A1* | 6/2017 | Sjolund | ............ G06N 20/00 |
| 2018/0221685 | A1* | 8/2018 | Eriksson | ............ G16H 50/20 |
| 2019/0074079 | A1* | 3/2019 | Zankowski | ............ G06K 9/6265 |
| 2019/0209867 | A1 | 7/2019 | Sun et al. | |
| 2020/0104695 | A1* | 4/2020 | Laaksonen | ............ A61N 5/1044 |
| 2020/0169085 | A1* | 5/2020 | Becher | ............ H02J 13/00 |
| 2020/0261744 | A1* | 8/2020 | Kumar | ............ A61N 5/1077 |
| 2021/0020297 | A1 | 1/2021 | Adler et al. | |
| 2021/0158929 | A1 | 5/2021 | Sjolund | |

FOREIGN PATENT DOCUMENTS

| WO | WO-2021009056 A1 | 1/2021 |
|---|---|---|
| WO | WO-2021009058 A1 | 1/2021 |

OTHER PUBLICATIONS

Banert, Sebastian, "Data-driven nonsmooth optimization", SIAM Journal on Optimization 30.1, (2020), 102-131.
Fine, Shai, "Efficient SVM training using low-rank kernel representations", Journal of Machine Learning Research 2. (Dec. 2001), 243-264.
(Continued)

*Primary Examiner* — Jason S Tiedeman
*Assistant Examiner* — Liza Tony Kanaan
(74) *Attorney, Agent, or Firm* — Schwegman Lundberg & Woessner, P.A.

(57) ABSTRACT

Techniques for solving a radiotherapy treatment plan optimization problem are provided. The techniques include receiving a first radiotherapy treatment plan optimization problem having a first set of parameters; processing the first set of parameters to estimate a second set of parameters of a second radiotherapy treatment plan optimization problem; generating a solution to the second radiotherapy treatment plan optimization problem based on the estimated second set of parameters; and generating a radiotherapy treatment plan based on the solution to the second radiotherapy treatment plan optimization problem.

25 Claims, 7 Drawing Sheets

(56) References Cited

OTHER PUBLICATIONS

Garnett, R., "Lecture 11: Bayesian Quadrature", University Lecture, [Online]. Retrieved from the Internet: https:www.cse.wustl.edu~garnett cse515t spring_2017 files lecture_notes 11.pdf, (2018), 4 pgs.

Provost, Serge B., "The exact distribution of indefinite quadratic forms in noncentral normal vectors", Annals of the Institute of Statistical Mathematics 48.2, (1996), 381-394.

Rodriguez-Lujan, Irene, "Quadratic programming feature selection", Journal of Machine Learning Research, (Apr. 2010), 26 pgs.

Sjolund, Jens, "A linear programming approach to inverse planning in Gamma Knife radiosurgery", Medical physics 46.4, (2019), 1533-1544.

Zaheer, Manzil, "Deep sets", Advances in neural information processing systems, (2017), 11 pgs.

"International Application Serial No. PCT EP2020 069588, International Search Report dated Oct. 14, 2020", 5 pgs.

"International Application Serial No. PCT EP2020 069588, Written Opinion dated Oct. 14, 2020", 6 pgs.

"International Application Serial No. PCT EP2020 069585, International Search Report dated Oct. 7, 2020", 5 pgs.

"International Application Serial No. PCT EP2020 069585, Written Opinion dated Oct. 7, 2020", 6 pgs.

"U.S. Appl. No. 16/512,972, Non Final Office Action dated Sep. 28, 2021", 19 pages.

"U.S. Appl. No. 16/512,972, Response filed Dec. 20, 2021 to Non Final Office Action dated Sep. 28, 2021", 11 pgs.

"U.S. Appl. No. 16/512,972, Final Office Action dated Jan. 20, 2022", 21 pgs.

\* cited by examiner

COMPRESSING RADIOTHERAPY TREATMENT PLAN OPTIMIZATION PROBLEMS

TECHNICAL FIELD

This disclosure relates generally to radiation therapy or radiotherapy optimization problems.

BACKGROUND

Radiotherapy is used to treat cancers and other ailments in mammalian (e.g., human and animal) tissue. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming, trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare.

Segmentation may be performed to identify the OARs and the area to be treated (for example, a planning target volume (PTV)). After segmentation, a dose plan may be created for the patient indicating the desirable amount of radiation to be received by the PTV (e.g., target) and/or the OARs. The PTV may have an irregular volume and may be unique as to its size, shape, and position. A treatment plan can be calculated after optimizing a large number of plan parameters to ensure that enough dose is provided to the PTV while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

Overview

In some embodiments, a computer-implemented method, non-transitory computer-readable medium, and a system comprising a memory and processor are provided for receiving, by processor circuitry, a first radiotherapy treatment plan optimization problem having a first set of parameters; processing, by the processor circuitry, the first set of parameters to estimate a second set of parameters of a second radiotherapy treatment plan optimization problem; generating, by the processor circuitry, a solution to the second radiotherapy treatment plan optimization problem based on the estimated second set of parameters; and generating, by the processing circuitry, a radiotherapy treatment plan based on the solution to the second radiotherapy treatment plan optimization problem.

In some implementations, the first and second sets of parameters comprise at least one of optimization variables, an objective function, or a set of constraints.

In some implementations, processing the first set of parameters comprises applying a machine learning model to the first set of parameters to estimate the second set of parameters, wherein the machine learning model is trained to establish a relationship between the second set of parameters and the first set of parameters of a plurality of training radiotherapy treatment plan optimization problems.

In some implementations, a first optimization variable in the first set of parameters is excluded from the second set of parameters.

In some implementations, the second set of parameters is smaller than the first set of parameters.

In some implementations, processing the first set of parameters comprises applying at least one of a non-linear functional relationship or a statistical model to the first set of parameters, wherein the statistical model comprises modeling the first set of parameters as random variables dependent on the second set of parameters and an objective function or constraint of the second radiotherapy treatment plan optimization problem is derived based on a measure of central tendency of the objective function or constraint of the first radiotherapy treatment plan optimization problem.

In some implementations, the second radiotherapy treatment plan optimization problem includes fewer constraints than the first radiotherapy treatment plan optimization problem.

In some implementations, a matrix in the second radiotherapy treatment plan optimization problem is sparse or structured in correspondence with a matrix in the first radiotherapy treatment plan optimization problem, and wherein generating the solution comprises processing the second radiotherapy treatment plan optimization problem using an optimization process.

In some implementations, the solution to the second radiotherapy treatment plan optimization problem is invariant or equivariant to permutations of first and second subsets of the first set of parameters.

In some implementations, the second radiotherapy treatment plan optimization problem has a fixed size relative to a size of the first radiotherapy treatment plan optimization problem.

In some implementations, the solution to the second radiotherapy treatment plan optimization problem approximates a solution to the first radiotherapy treatment plan optimization problem.

In some implementations, the first radiotherapy treatment plan optimization problem comprises at least one of a linear programming problem or a quadratic programming problem, and wherein the first and second sets of parameters are related through a Gaussian process.

In some implementations, the computer-implemented method, non-transitory computer-readable medium, and a system comprising a memory and processor are provided for computing a second parameter of the second set of parameters based on a point estimate corresponding to a Gaussian distribution of a first parameter in the first set of parameters;

and replacing the first parameter in the first set of parameters with the second parameter to generate the second radiotherapy treatment plan optimization problem, wherein the second radiotherapy treatment plan optimization problem comprises another linear or quadratic programming problem.

In some implementations, the computer-implemented method, non-transitory computer-readable medium, and a system comprising a memory and processor are provided for marginalizing the first set of parameters over a Gaussian distribution to estimate the second set of parameters.

In some implementations, the computer-implemented method, non-transitory computer-readable medium, and a system comprising a memory and processor are provided for mapping the solution to the second radiotherapy treatment plan optimization problem onto a space of the first set of parameters of the first radiotherapy treatment plan optimization problem.

In some implementations, mapping the solution onto the space of the first set of parameters comprises applying a machine learning model to the solution to estimate another solution to the first radiotherapy treatment plan optimization problem.

In some implementations, the first and second radiotherapy treatment plan optimization problems are processed by an optimization process until a predetermined criterion is met.

In some embodiments, a computer-implemented method, non-transitory computer-readable medium, and a system comprising a memory and processor are provided for training a machine learning model to solve a radiotherapy treatment plan optimization problem, by: receiving, by processor circuitry, a plurality of first training radiotherapy treatment plan optimization problems, each of the plurality of the first training radiotherapy treatment plan optimization problems comprising a first set of parameters; and training, by the processor circuitry, the machine learning model to generate an estimate of a second set of parameters of a second radiotherapy treatment plan optimization problem by establishing a relationship between the second set of parameters and the first set of parameters of the plurality of the first training radiotherapy treatment plan optimization problems.

In some implementations, the machine learning model is trained in a supervised approach by: obtaining a first training data pair comprising a given one of the first set of parameters and a corresponding solution to a given one of the plurality of first training radiotherapy treatment plan optimization problems; processing the given one of the first set of parameters with the machine learning model to generate the estimate of the second set of parameters of the second radiotherapy treatment plan optimization problem; solving the second radiotherapy treatment plan optimization problem based on the estimate of the second set of parameters to generate a given solution to the second radiotherapy treatment plan optimization problem; computing a deviation between at least one of: (1) the given solution and the corresponding solution or (2) a decoded version of the given solution in a space of the given one of the plurality of first training radiotherapy treatment plan optimization problems and the corresponding solution; and updating parameters of the machine learning model based on the computed deviation.

In some implementations, the machine learning model is trained in an unsupervised approach by: obtaining a given one of the first set of parameters; processing the given one of the first set of parameters with the machine learning model to generate the estimate of the second set of parameters of the second radiotherapy treatment plan optimization problem; solving the second radiotherapy treatment plan optimization problem based on the estimate of the second set of parameters to generate a given solution to the second radiotherapy treatment plan optimization problem; computing a metric of the given solution; and updating parameters of the machine learning model based on the computed metric.

In some implementations, the metric comprises a statistical metric representing a likelihood of observing training data or a utility of a treatment plan corresponding to the given solution.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
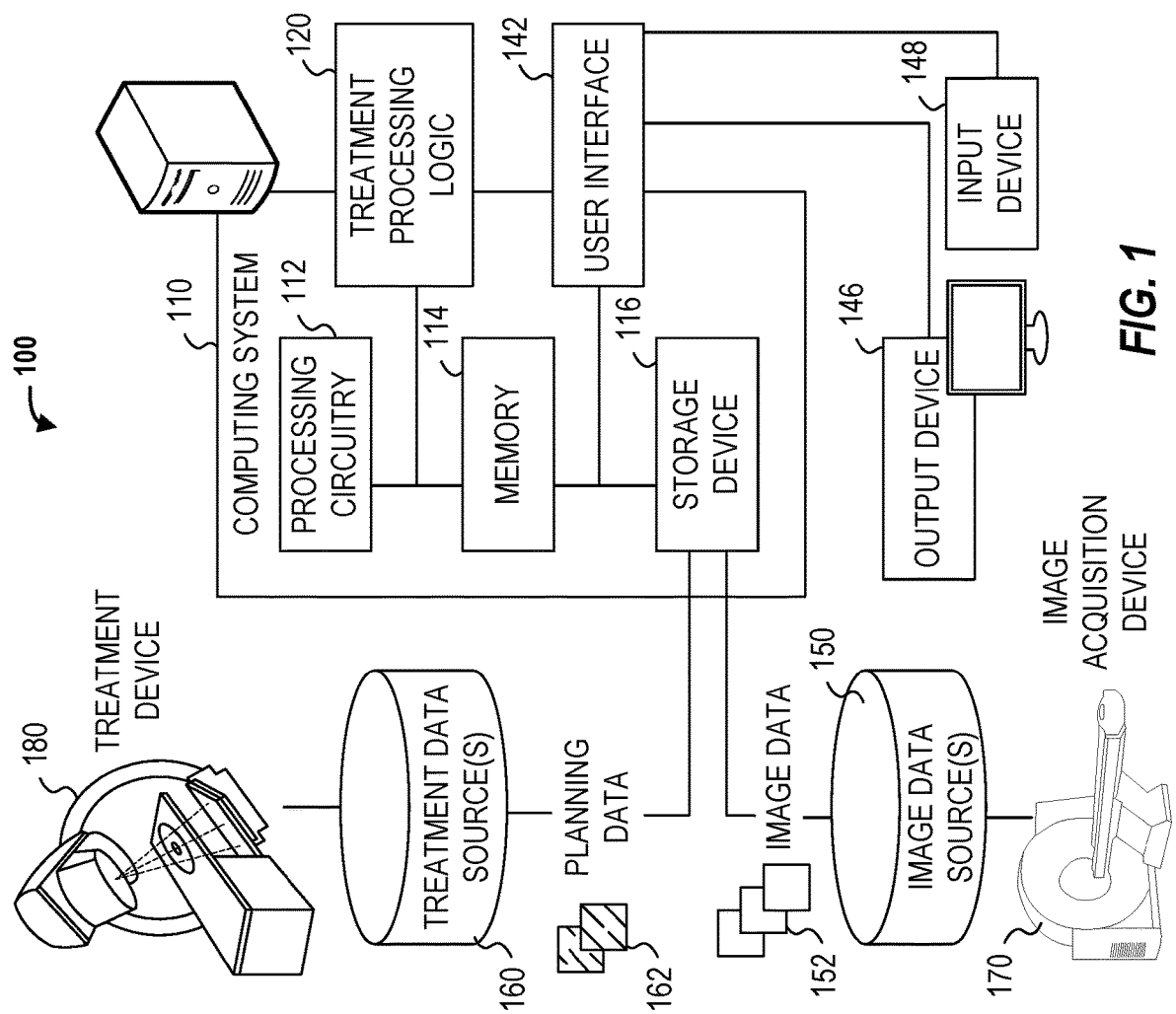
FIG. 1 illustrates an exemplary radiotherapy system adapted for performing treatment plan generation processing, according to some examples.

The present disclosure includes various techniques to generate radiotherapy treatment plans by simplifying a first radiotherapy treatment plan optimization problem into a second radiotherapy optimization problem that is less complex than the first radiotherapy treatment plan optimization problem. Particularly, parameters of the first radiotherapy treatment plan optimization problem are processed to estimate parameters of a second radiotherapy treatment plan optimization problem and a solution to the second radiotherapy treatment plan optimization problem is generated and used to provide the radiotherapy treatment plan. In some embodiments, the parameters of the first radiotherapy treatment plan optimization problem are processed by a machine learning model to estimate the parameters of the second radiotherapy treatment plan optimization problem. In some embodiments, the parameters of the first radiotherapy treatment plan optimization problem are modeled by a statistical function or non-linear functional relationship to estimate the parameters of the second radiotherapy treatment plan optimization problem.

The technical benefits include reduced computing processing times to generate radiotherapy treatment plans and solving radiotherapy treatment plan optimization problems and accompanying improvements in processing, memory, and network resources used to generate radiotherapy treatment plans and solve radiotherapy treatment plan optimization problems. These radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

Radiotherapy is one of the primary methods for treating cancer and is recommended for over 50% of all cancer patients. Treatment plans are created through a complex design process involving a mathematical optimization problem that captures the desirable characteristics of the dose delivery—typically requiring a sufficiently high dose to the target while minimizing the dose to healthy tissue. The overall structure of the optimization problem is the same for most forms of radiotherapy, including linac-based treatments (3D-CRT, IMRT, VMAT), proton treatments, Gamma Knife radiosurgery, and brachytherapy. The end result is the radiotherapy device configuration (e.g., control points) required to deliver the dose distribution.

Current planning software typically solve the minimization problem using standard mathematical optimization methods. These can be slow, causing unnecessary waiting for patients and clinicians. Future applications utilizing real-time imaging could even require real-time treatment planning, which cannot be performed using conventional optimization problem solvers.

The disclosed techniques address these challenges and increase the speed and efficiency at which radiotherapy treatment plan optimization problems are solved by leveraging a ML model, a functional relationship, and/or a statistical model to convert a complex first radiotherapy treatment plan optimization problem with a first set of optimization problem parameters (e.g., optimization variables, an objective function, and/or a set of constraints) to a less complex second radiotherapy treatment plan optimization problem with a second set of optimization problem parameters (optimization variables, an objective function, and/or a set of constraints). In some embodiments, the ML model is used to process parameters of a first radiotherapy treatment plan optimization problem and to estimate parameters of a second radiotherapy treatment plan optimization problem, which simplifies and allows the radiotherapy treatment plan optimization problem to be solved much faster. In such cases, the second radiotherapy treatment plan optimization problem may have a less complex optimization function, fewer constraints, and/or fewer decision variables than the first radiotherapy treatment plan optimization problem, making it less complex to solve. In some embodiments, the parameters of the first radiotherapy treatment plan optimization problem are functionally and/or statistically modeled to generate the parameters of the second radiotherapy treatment plan optimization problem. In such cases, the optimization function of the second radiotherapy treatment plan optimization problem may have the same structure and form as the first radiotherapy treatment plan optimization problem but may have fewer decision variables and/or constraints, which makes it less complex to solve.

In some cases, the solution to the second radiotherapy treatment plan optimization problem estimates the solution to the first radiotherapy treatment plan optimization problem and can be used directly to generate the radiotherapy treatment plan. In some cases, the solution to the second radiotherapy treatment plan optimization problem can be decoded to solve the first radiotherapy treatment plan optimization problem to generate the radiotherapy treatment plan. In some embodiments, the first and/or second radiotherapy treatment plan optimization problem is solved using a process discussed in commonly-assigned Jens Sjolund et al., U.S. Patent Application Ser. No. 16/512,972, filed concurrently herewith, entitled "OPTIMIZATION OF RADIOTHERAPY TREATMENT PLANS USING MACHINE LEARNING", which is hereby incorporated by reference. According to the disclosed techniques, by increasing the speed at which radiotherapy treatment plan optimization problems are solved, the disclosed techniques may enable real-time treatment planning to be performed and reduce wait time for patients and clinicians.

Specifically, the disclosed techniques receive a first radiotherapy treatment plan optimization problem having a first set of parameters and process the first set of parameters to estimate a second set of parameters of a second radiotherapy treatment plan optimization problem. The disclosed techniques generate a solution to the second radiotherapy treatment plan optimization problem based on the estimated second set of parameters and generate a radiotherapy treatment plan based on the solution to the second radiotherapy treatment plan optimization problem. Machine settings, e.g. control points, of a radiotherapy treatment device can then be determined and generated by the solution to the second radiotherapy treatment plan optimization problem and/or based on an estimated solution of the first radiotherapy treatment plan optimization problem corresponding to the solution to the second radiotherapy treatment plan optimization problem.

As referred to throughout this disclosure, the "first optimization problem" is an original optimization problem for a given radiotherapy treatment plan that needs to be simplified. The "second optimization problem" is a simplified version of the first optimization problem that is solved to generate the given radiotherapy treatment plan information.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of the treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

As an example, the radiotherapy processing computing system 110 can be configured to receive a treatment goal of a subject (e.g., from one or more MR images) and generate a radiotherapy treatment plan by executing instructions or data from the treatment processing logic 120, as part of operations to generate treatment plans to be used by the treatment device 180 and/or for output on device 146. In an embodiment, the treatment processing logic 120 solves an optimization problem to generate the radiotherapy treatment plan. The treatment processing logic 120 solves the radiotherapy optimization problem by simplifying a first radiotherapy treatment plan optimization problem into a second radiotherapy optimization problem that is less complex than the first radiotherapy treatment plan optimization problem. In some cases, a first optimization variable in the first set of parameters is excluded from the second set of parameters. In some cases, the second set of parameters is smaller than the first set of parameters. In some cases, the second radiotherapy treatment plan optimization problem includes fewer constraints than the first radiotherapy treatment plan optimization problem. In some cases, the second radiotherapy treatment plan optimization problem has a fixed size relative to a size of the first radiotherapy treatment plan optimization problem.

In some cases, the second radiotherapy treatment plan optimization problem includes parameters that are defined or selected from class of optimization problems for which there exist more efficient algorithms to solve than the parameters of the first optimization problem. For example, the second optimization problem may be convex whereas the first optimization problem is non-convex. As another example, the second optimization problem may be unconstrained whereas the first optimization problem is constrained. As another example, the second optimization problem may be a semidefinite programming problem whereas the first optimization problem is a general nonlinear problem. As another example, the second optimization problem may be defined or solved by linear programming whereas the first optimization problem is defined or solved by quadratic programming. In some cases, the second optimization problem may be less complex than the first optimization problem because the second optimization problem enables efficient linear algebra routines (e.g. sparse linear algebra or certain matrix factorizations).

In some embodiments, parameters of the first radiotherapy treatment plan optimization problem are processed to estimate parameters of a second radiotherapy treatment plan optimization problem and a solution to the second radiotherapy treatment plan optimization problem is generated and used to provide the radiotherapy treatment plan. In some embodiments, the parameters of the first radiotherapy treatment plan optimization problem are processed by a machine learning model to estimate the parameters of the second radiotherapy treatment plan optimization problem. In some embodiments, the parameters of the first radiotherapy treatment plan optimization problem are modeled by a statistical function or non-linear functional relationship to estimate the parameters of the second radiotherapy treatment plan optimization problem.

In treatment planning, a clinical decision maker wrestles with the physical limitations of the radiotherapy equipment to find an acceptable compromise for the patient. In most cases this interaction is mediated by an optimization problem. The overall structure of these optimization problems is the same for most forms of radiotherapy, including linac-based treatments (3D-CRT, IMRT VMAT), proton treatments, Gamma Knife radiosurgery and brachytherapy. The inventive subject matter presented here is applicable to all of them.

The biological effect of the radiotherapy treatment depends on the absorbed dose d. The radiotherapy equipment differ in the way they deliver the dose, but the relation can usually be modelled (at least approximately) as a linear function $d(x)=\Phi x$, where $\Phi$ is a dose influence matrix that maps from the decision variables x to dose. Typically, the objective function $f$ and at least some of the constraints $c_i$ are formulated only in terms of dose. The physical meaning of the decision variables depends on the treatment modality, e.g., it is irradiation time in Gamma Knife radiosurgery and brachytherapy whereas it is fluence in linac treatments. Commonly both the elements in the dose influence matrix and the decision variables are non-negative.

The dose influence matrix $\Phi$ is often static during the optimization, which means that it could be precomputed and stored. A typical optimization problem in radiotherapy thus has the form defined by Equation 1:

$$\begin{aligned} & \underset{x,d}{\text{minimize}} && f(d) \\ & \text{subject to} && d = \Phi x, \\ &&& x \geq 0, \\ &&& c_i(x) \leq 0, \, i \in C_x \\ &&& c_i(d) \leq 0, \, i \in C_d \end{aligned} \quad (1)$$

where $C_x$ and $C_d$ denote the set of machine constraints and dose constraints, respectively. However, what constraint functions $\{c_i\}$ that are relevant depends on the application. The functions $f$ and $c_i$ can be both nonlinear and nonconvex (or even integer valued). Two examples of complicated optimization problems arise from isocenter selection in Gamma Knife radiosurgery or arc sequencing in VMAT planning. In such cases, the optimization problem can be solved either directly (e.g., direct aperture optimization in VMAT planning) or indirectly (e.g., via a sequence of increasingly difficult subproblems). Regardless, the most complex optimization problem typically dominates the total runtime.

A generic radiotherapy treatment plan optimization problem can be expressed according to Equation 2:

$$\begin{aligned} & \underset{x}{\text{minimize}} && f(x) \\ & \text{subject to} && x \in X, \end{aligned} \quad (2)$$

for some general feasible set X This generic radiotherapy treatment plan optimization problem can often be written more explicitly as Equation 3:

$$\underset{x}{\text{minimize}} \quad f(x) \quad (3)$$

-continued $$\text{subject to } c_i(x) = 0, i \in \varepsilon$$
$$c_i(x) \geq 0, i \in I$$

where $f$ is the objective function, x are the optimization variables and $\{c_i\}$ is a set of functions where $\varepsilon$ and I are the sets of indices corresponding to equality and inequality constraints, respectively. According to the disclosed techniques, solving such optimization problems is made less complex by using the parameters of the original optimization problems to estimate one or more parameters (e.g., x, $f$ and/or $\{c_i\}$) of a second, less complex, optimization problem and then applying the conventional methods to solve the less complex optimization problem.

The original radiotherapy treatment plan optimization problems are difficult, computationally inefficient, and/or take an unacceptable amount of time to solve because they are large or because they have a complicated structure (e.g., non-differentiable, non-convex or mixed-integer). According to some embodiments, the complexity of solving the original radiotherapy treatment plan optimization problems is simplified to reduce computational resources needed and computation time for solving the problems. One such way includes approximating the original radiotherapy treatment plan optimization problem with another radiotherapy treatment plan optimization problem that has the same structure but fewer decision variables and/or constraints. Another way includes approximating the original radiotherapy treatment plan optimization problem with another radiotherapy treatment plan optimization problem that has a simpler structure, e.g., a convex relaxation of a non-convex problem. In both cases, parameters of the original radiotherapy treatment plan optimization problem are used to estimate parameters of another radiotherapy treatment plan optimization problem that is less complicated to solve. In some embodiments, this parameters are estimated according to a statistical relationship among the parameters and/or a functional relationship among the parameters.

In some embodiments, a machine learning model is utilized to generate the parameters of the less complex radiotherapy treatment plan optimization problem from the parameters of the original radiotherapy treatment plan optimization problem. In such cases, variable size parameters of the radiotherapy treatment plan optimization problem are expressed as a fixed size representation using a machine learning model.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor rather than a general-purpose processor. The processing circuitry 112 may include one or more known processing devices, such as a microprocessor from the Pentium™, Core™ Xeon™, or Itanium® family manufactured by Intel™, the Turion™, Athlon™ Sempron™, Opteron™, FX™, Phenom™ family manufactured by AIVID™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of the ML model(s) of the disclosed embodiments), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data as a result of a treatment plan generated by the treatment processing logic 120. The image data source 150 may also provide or host the imaging data for use in the treatment processing logic 120.

In an example, computing system 110 may communicate with treatment data source(s) 160 and input device 148 to generate pairs of one or more training solutions to first training radiotherapy treatment plan optimization problems and a plurality of training parameters of the first training radiotherapy treatment plan optimization problems.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120 to generate a treatment plan. Particularly, treatment processing logic 120 receives an optimization problem that is derived based on the medical images that are received. The treatment processing logic processes parameters of the received optimization problem to estimate parameters of a less complex second optimization problem. Once the parameters are estimated, the second optimization problem is solved and used to generate a treatment plan.

In addition, the processing circuitry 112 may utilize software programs to generate intermediate data such as updated parameters to be used, for example, by a neural network (NN) model, machine learning model, treatment processing logic 120 or other aspects involved with generation of a treatment plan as discussed herein. Further, such software programs may utilize the treatment processing logic 120 to produce new or updated treatment plan parameters for deployment to the treatment data source 160 and/or presentation on output device 146, using the techniques further discussed herein. The processing circuitry 112 may subsequently then transmit the new or updated treatment plan parameters via a communication interface and the network to the treatment device 180, where the radiation therapy plan will be used to treat a patient with radiation via the treatment device 180, consistent with results of the trained ML model implemented by the treatment processing logic 120 (e.g., according to the processes discussed below in connection with FIG. 3).

In the examples herein, the processing circuitry 112 may execute software programs that invoke the treatment processing logic 120 to implement functions of ML, deep learning, NNs, and other aspects of artificial intelligence for treatment plan generation from an input radiotherapy medical information (e.g., CT image, MR image, and/or sCT image and/or dose information). For instance, the processing circuitry 112 may execute software programs that train, analyze, predict, evaluate, and generate a treatment plan parameter from received radiotherapy medical information as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system 100.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The treatment processing logic 120 in the radiotherapy processing computing system 110 implements a ML model, which involves the use of a trained (learned) ML model. This ML model may be provided by a NN trained as part of a NN model. One or more teacher ML models may be provided by a different entity or at an off-site facility relative to treatment processing logic 120 and is accessible by issuing one or more queries to the off-site facility.

Machine learning (ML) algorithms or ML models or techniques can be summarized as function approximation. Training data consisting of input-output pairs of some type (e.g., one or more training optimization variables and training parameters of a plurality of training radiotherapy treatment plan optimization problems) are acquired from, e.g., expert clinicians or prior optimization plan solvers and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as:

$$\min_\theta \sum_{m=1}^{M} \|A_\theta(x_m) - y_m\|^2$$

Once the network has been trained (e.g., $\theta$ has been selected), the function $A_\theta$ can be applied to any new input. For example, in the above setting of radiotherapy treatment plan optimization problem parameters, parameters of a never-before-seen radiotherapy treatment plan optimization problem can be fed into $A_\theta$, and parameters of another, less complex, radiotherapy treatment plan optimization problem are estimated.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function $y=f(x)$ including non-linear functions. In ML, an assumption is that the training and test data are both generated by the same data-generating process, $p_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2A:
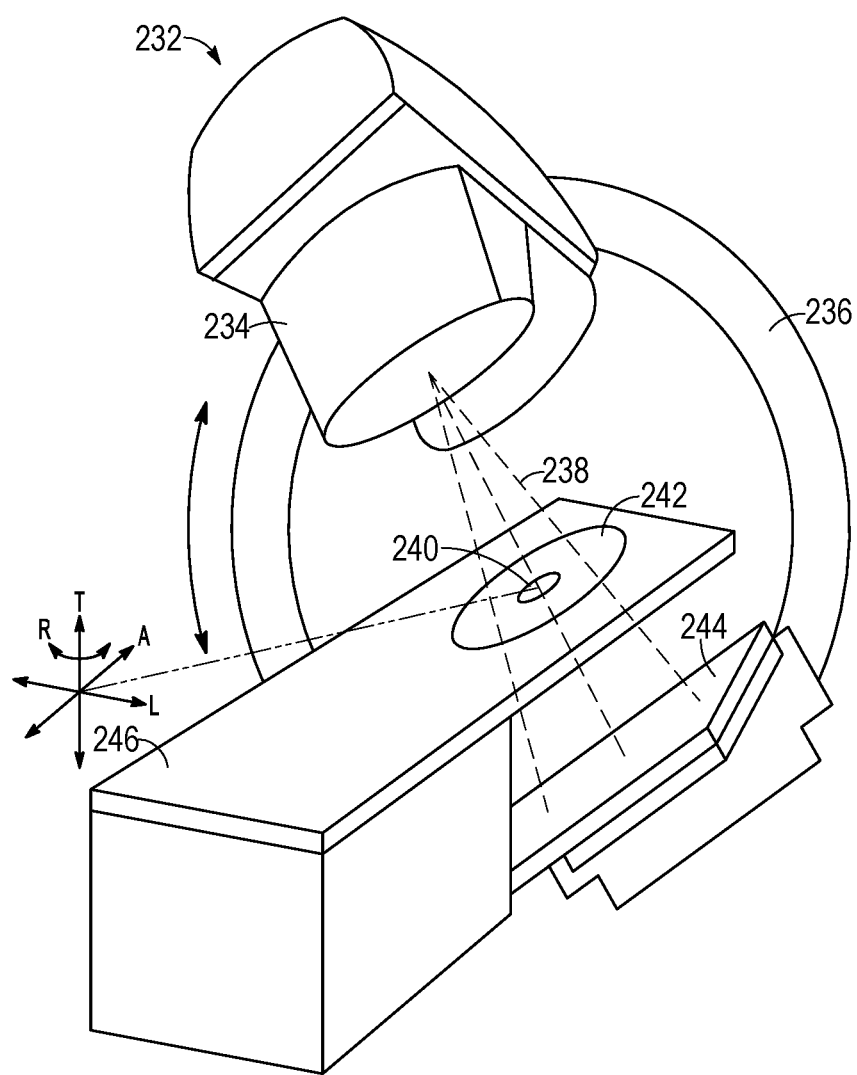
FIG. 2A illustrates an exemplary image-guided radiotherapy device, according to some examples of the disclosure.

FIG. 2A illustrates an exemplary image-guided radiation therapy device 242 that includes a radiation source, such as an X-ray source or a linear accelerator, a couch 246, an imaging detector 244, and a radiation therapy output 234. The radiation therapy device 232 may be configured to emit a radiation therapy beam 238 to provide therapy to a patient. The radiation therapy output 234 can include one or more attenuators or collimators, such as a MLC.

As an example, a patient can be positioned in a region 242, supported by the treatment couch 246, to receive a radiation therapy dose according to a radiation therapy treatment plan. The radiation therapy output 234 can be mounted or attached to a gantry 236 or other mechanical support. One or more chassis motors (not shown) may rotate the gantry 236 and the radiation therapy output 234 around the couch 246 when the couch 246 is inserted into the treatment area. In an example, gantry 236 may be continuously rotatable around couch 246 when the couch 246 is inserted into the treatment area. In another example, gantry 236 may rotate to a predetermined position when the couch 246 is inserted into the treatment area. For example, the gantry 236 can be configured to rotate the therapy output 234 around an axis ("A"). Both the couch 246 and the radiation therapy output 234 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 246's movements or rotations in order to properly position the patient in or out of the radiation therapy beam 238, according to a radiation therapy treatment plan. Both the couch 246 and the gantry 236 are independently moveable from one another in multiple degrees of freedom, which allows the patient to be positioned such that the radiation therapy beam 238 can precisely target the tumor.

The coordinate system (including axes A, T, and L) can have an origin located at an isocenter 240. The isocenter 240 can be defined as a location where the central axis of the radiation therapy beam 238 intersects the origin of a coordinate axis, such as to deliver a prescribed radiation dose to a location on or within a patient. Alternatively, the isocenter 240 can be defined as a location where the central axis of the radiation therapy beam 238 intersects the patient for various rotational positions of the radiation therapy output 234 as positioned by the gantry 236 around the axis A.

Gantry 236 may also have an attached imaging detector 244. The imaging detector 244 is preferably located opposite to the radiation source (output 234) and, in an example, the imaging detector 244 can be located within a field of the therapy beam 238. The imaging detector 244 can be mounted on the gantry 236, preferably opposite the radiation therapy output 234, so as to maintain alignment with the radiation therapy beam 238. The imaging detector 244 rotates about the rotational axis as the gantry 236 rotates. In an example, the imaging detector 244 can be a flat panel detector (e.g., a direct detector or a scintillator detector). In this manner, the imaging detector 244 can be used to monitor the radiation therapy beam 238, or the imaging detector 244 can be used for imaging the patient's anatomy, such as portal imaging. The control circuitry of radiation therapy device 232 may be integrated within the radiotherapy system 100 or remote from it.

In an illustrative example, one or more of the couch 246, the therapy output 234, or the gantry 236 can be automatically positioned, and the therapy output 234 can establish the therapy beam 238 according to a specified dose for a particular therapy delivery instance. A sequence of therapy deliveries can be specified according to a radiation therapy treatment plan, such as using one or more different orientations or locations of the gantry 236, couch 246, or therapy output 234. The therapy deliveries can occur sequentially but can intersect in a desired therapy locus on or within the patient, such as at the isocenter 240. A prescribed cumulative dose of radiation therapy can thereby be delivered to the therapy locus while damage to tissue nearby the therapy locus can be reduced or avoided.

Thus, FIG. 2A specifically illustrates an example of a radiation therapy device 232 operable to provide radiotherapy treatment to a patient consistent with or according to a radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

Figure 2B:
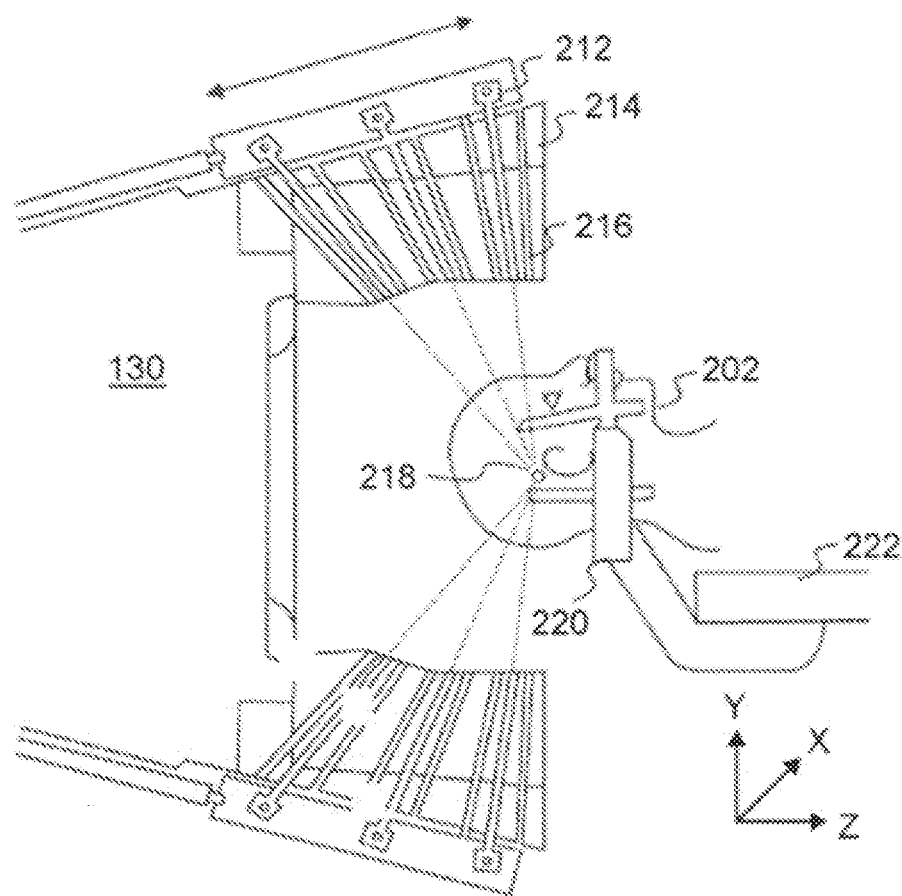
FIG. 2B illustrates a radiation therapy device, a Gamma Knife, according to some examples of the disclosure.

FIG. 2B illustrates a radiotherapy device 130, a Gamma Knife in which the present disclosure can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

According to some embodiments, a class of optimization problems can be parameterized by input parameters $u \in U$ that could, for example, correspond to the objective function $f$ and the constraint functions $c_i$. As an example, any linear programming problem can be equivalently expressed in standard form, where the objective function is determined by a cost vector w and the constraint functions are determined by a constraint matrix A together with a constraint vector b (though the details depend on the convention used), so in some embodiments the input parameters $u = \{w, A, b\}$.

A given choice of parameters u defines an optimization problem, for example by a mapping $F(u) = \{f, X\}$ where $f$ is the objective function and X the set of feasible points. Assuming that there are points that satisfy the constraint (e.g., that X is not empty), then (local) solutions to the optimization problem are defined as the set of points $x^* \in X$ such that $f(x^*) \leq f(x)$ for all feasible x in a neighbourhood of $x^*$. The solution may not be unique. According to some embodiments, solving an optimization problem includes finding at least one point $x^*$ that is a solution to the optimization problem or is within a specified tolerance of a solution to the optimization problem.

A loss function may be used to quantify how far a point x is from being a solution to the first optimization problem. One example, relevant if x and $x^*$ are points in a normed vector space and $x^*$ is unique, is to use the induced metric $l(x, x^*) = \|x - x^*\|$, where the norm $\|.\|$ could be a p-norm. Alternatively, x can be projected onto the feasible set X before evaluating the loss. An alternative is to directly use the objective function value of the first optimization problem as a loss function l(x). A variation is to use the objective function value (or current iteration in a loss) of the first optimization problem after it has been processed by an optimization algorithm, e.g., for a fixed number of iterations, or until convergence (in which case the loss quantifies how good the local solution that is found after starting at x is).

To illustrate the disclosed embodiments, T is used to encode the process of solving an optimization problem according to Equation 4:

$$T[\{f, X\}] = \underset{x \in X}{\mathrm{argmin}}\, f(x) \qquad (4)$$

In this way, the original (first) optimization problem can be formulated compactly as searching for a point $x^*(u)$ in the image of $T \circ F(u)$ according to Equation 5:

$$x^* \in T[F(u)] = \underset{x \in X}{\mathrm{argmin}}\, f(x) \qquad (5)$$

As explained above, the original (first) optimization problem may be difficult and complex to solve and work with because it takes a large effort to solve and because of its variable size and ordering. As such, according to some embodiments, a second, more convenient, simplified, and less complex optimization problem is formulated by treatment processing logic 120, such as using a mapping $G(u) = \{g, Z\}$ that is different from F(u) according to Equation 6:

$$z^* \in T[G(u)] = \underset{z \in Z}{\mathrm{argmin}}\, g(z) \qquad (6)$$

The mapping $G(u) = \{g, Z\}$ that defines the relationship between the parameters of the second optimization problem and the original optimization problem can be generated or provided by an ML model, a non-linear functional relationship, and/or a statistical model. Specifically, the behavior of a mapping G, encoder $h_{enc}$ (that maps the parameters of the first optimization problem to the parameters of the second optimization problem) and/or decoder $h_{dec}$ (that maps the parameters of the second optimization problem to the parameters of the first optimization problem) could be controlled by the treatment processing logic 120 retrieving or generating a set of parameters θ. In some embodiments, some of these parameters θ are computed or estimated by treatment processing logic 120 based on a non-linear functional relationship or a statistical model. The statistical model models the first set of parameters as random variables dependent on the second set of parameters and an objective function or constraint of the second radiotherapy treatment plan optimization problem is derived based on a measure of central tendency of the objective function or constraint of the first radiotherapy treatment plan optimization problem.

In some embodiments, as shown and described in connection with FIG. 3, some of these parameters θ could be selected by treatment processing logic 120 and estimated using an ML model that is trained on a dataset of other treatment plans. In such cases, if both G and $h_{dec}$ are parameterized they could be trained jointly by treatment processing logic 120. The training could be performed in a supervised fashion, e.g. with data consisting of M pairs $\{(u_m, x_m^*)\}_{m=1}^{M}$ and the aim to select θ to minimize the expected loss over the dataset. Equation 7 shows how the θ parameters are computed in a supervised fashion:

$$\theta^* = \underset{\theta \in \Theta}{\operatorname{argmin}} \sum_{m=1}^{M} \ell(h_{dec}(T[G(u_m)], x_m^*). \quad (7)$$

A corresponding expression when training in an unsupervised fashion, e.g., with data consisting of M problem instances $\{u_m\}_{m=1}^{M}$, is provided according to Equation 8:

$$\theta^* = \underset{\theta \in \Theta}{\operatorname{argmin}} \sum_{m=1}^{M} \ell(h_{dec}(T[G(u_m)])). \quad (8)$$

In such cases, the aim of the training could also be to maximize a statistical metric, such as the likelihood of observing the training data, or to maximize (a proxy for) the utility of the treatments plan generated based on the training data.

In some embodiments, a solution z* to the second optimization problem could be useful in its own right, so that a treatment plan may be generated by treatment processing logic 120 based on the solution z*. The procedure defining the second optimization problem could be designed to maximize the utility of z* in generating a treatment plan. In some embodiments, z* (the solution to the second optimization problem) can be decoded by treatment processing logic 120 to map the solution to the same space as the parameters (e.g., the optimization variables) of the original first optimization problem. In some implementations, the decoding is performed by treatment processing logic 120 using a function $h_{dec}(z)$. In some cases, the function $h_{dec}$ is generated by treatment processing logic 120 in a way such that when the solution to the second optimization problem is applied to the function $h_{dec}(z^*)$, the result approximately solves the original first optimization problem. Similarly, an encoder can be used to map parameters (e.g., optimization variables) from the first optimization problem to the second optimization problem.

Figure 3:
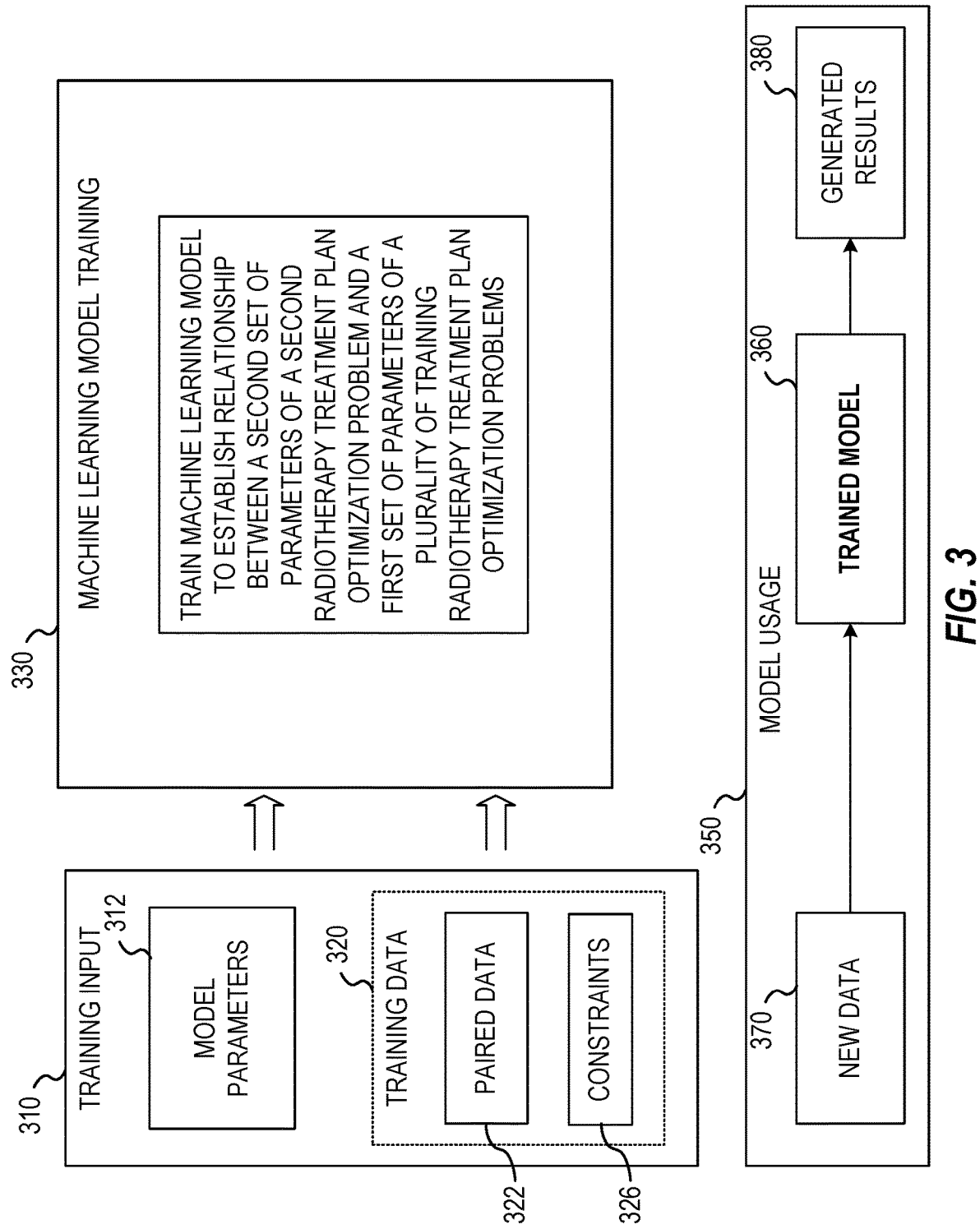
FIG. 3 illustrates an exemplary data flow for training and use of a machine learning technique to estimate parameters of a second radiotherapy treatment plan optimization problem from parameters of a first radiotherapy treatment plan optimization problem, according to some examples of the disclosure.

FIG. 3 illustrates an exemplary data flow for training and use of a machine learning model to estimate parameters of a second radiotherapy treatment plan optimization problem from parameters of a first radiotherapy treatment plan optimization problem, according to some examples of the disclosure. The data flow includes training input 310, ML model (technique) training 330, and model usage 350.

Training input 310 includes model parameters 312 and training data 320, which may include paired training data sets 322 (e.g., input-output training pairs) and constraints 326. Model parameters 312 store or provide the parameters or coefficients of machine learning model $Â_θ$. During training, these parameters 312 are adapted based on the input-output training pairs of the training data sets 322. After the parameters 312 are adapted (after training), the parameters are used by trained treatment models 360 to implement the trained machine learning model $Â_θ$ on a new set of data 370.

Training data 320 includes constraints 326, which may define the physical constraints of a given radiotherapy device or constraints of the first or second optimization problems. The paired training data sets 322 may include sets of input-output pairs, such as pairs of solutions to a first plurality of first radiotherapy treatment plan optimization problems and parameters of the first plurality of first radiotherapy treatment plan optimization problems. Some components of training input 310 may be stored separately at a different off-site facility or facilities than other components.

Machine learning model(s) training 330 trains one or more machine learning techniques $Â_θ$ based on the sets of input-output pairs of paired training data sets 322. For example, the model training 330 may train the ML model parameters 312 by minimizing a first loss function based on one or more solutions to a first plurality of first radiotherapy treatment plan optimization problems and the corresponding training parameters of the first plurality of first radiotherapy treatment plan optimization problems.

The result of minimizing the loss function for multiple sets of training data trains, adapts, or optimizes the model parameters 312 of the corresponding ML models. In this way, the ML model is trained to establish a relationship between parameters of a second radiotherapy treatment plan optimization problem and parameters of the plurality of the first training radiotherapy treatment plan optimization problems.

As an example, the ML model may be trained according to supervised learning techniques. In such cases, to train the ML model $Λ_θ$, a plurality of training optimization problems that have previously been solved for other patients (and/or that include synthetically generated problems) are retrieved together with their corresponding training parameters (e.g., optimization variables and solutions). Specifically, a first training data batch that includes a batch of the parameters of a first training radiotherapy treatment plan optimization problem and a corresponding batch of solutions to the first training radiotherapy treatment plan optimization problem is obtained. As another example, the first training data batch includes a batch of the parameters of multiple first training radiotherapy treatment plan optimization problems and a corresponding batch of solutions to the multiple first training radiotherapy treatment plan optimization problems. The batch of the training data can be used to train the ML model with the same parameters of the ML model and may range from one set of parameters of the first training radiotherapy treatment plan optimization problem and a corresponding solution to the first training radiotherapy treatment plan optimization problem to all of the training problems and solutions. The given batch of the parameters is processed with the ML model to generate the estimate of the parameters of the second radiotherapy treatment plan optimization problem. For example, the ML model is applied by treatment processing logic 120 to the first training data batch to compute the mapping G(u)={g,Z}. The second radiotherapy treatment plan optimization problem is solved by treatment processing logic 120 based on the estimate of the parameters of the second radiotherapy treatment plan optimization problem to generate a given solution to the second radiotherapy treatment plan optimization problem. For example, the second radiotherapy treatment plan optimization problem is solved to compute $$z^* \in T[G(u)] = \underset{z \in Z}{\mathrm{argmin}}\, g(z).$$

A deviation is computed between at least one of: (1) the given solution z* and the corresponding solution x* or (2) a decoded version of the given solution $h_{dec}(z^*)$ in a space of the given batch of the first training radiotherapy treatment plan optimization problem and the corresponding solution x*. Parameters of the machine learning model are updated based on the computed deviation.

The ML model is then applied with the updated parameters by treatment processing logic 120 to another batch of the training data to again estimate a given set of parameters of the second radiotherapy treatment plan optimization problem to compute a deviation in a similar manner as the first batch and update parameters of the ML model. Parameters of the ML model are again updated and iterations of this training process continue for a specified number of iterations or epochs or until a given convergence criteria has been met.

The ML model may be trained by treatment processing logic 120 according to unsupervised learning techniques. Unsupervised learning techniques assume that the true solution is unknown. In such cases, to train the ML model $\Lambda_\theta$, training data is obtained that includes a given batch of the parameters of the first training radiotherapy treatment plan optimization problem. The batch of the parameters of the first training radiotherapy treatment plan optimization problem can be used to train the ML model with the same parameters of the ML model and may range from one set of parameters of the first training radiotherapy treatment plan optimization problem to all of the parameters of the first training radiotherapy treatment plan optimization problem. The given batch of the parameters that is obtained is processed by treatment processing logic 120, with the ML model to generate an estimate of the parameters of the second radiotherapy treatment plan optimization problem. The second radiotherapy treatment plan optimization problem is solved by treatment processing logic 120 based on the estimate of the parameters of the second radiotherapy treatment plan optimization problem to generate a given solution to the second radiotherapy treatment plan optimization problem. For example, the second radiotherapy treatment plan optimization problem is solved to compute $$z^* \in T[G(u)] = \underset{z \in Z}{\mathrm{argmin}}\, g(z).$$

A metric of the given solution z* is computed. Based on this metric, updated parameters for the ML model are computed by treatment processing logic 120.

The ML model is then applied with the updated parameters by treatment processing logic 120 to another batch of the parameters of the first training radiotherapy treatment plan optimization problem to again estimate a given set of parameters of the second radiotherapy treatment plan optimization problem and to generate a solution to the second radiotherapy treatment plan optimization problem. Parameters of the ML model are again updated and iterations of this training process continue for a specified number of epochs or until all of the batches of the parameters of the first training radiotherapy treatment plan optimization problem are processed.

After the machine learning model $\hat{A}_\theta$ (sometimes referred to as $\Lambda_\theta$) is trained, new data 370, including one or more patient input parameters (e.g., a radiotherapy treatment plan optimization problem), may be received. The trained machine learning technique $\hat{A}_\theta$ may be applied to the new data 370 to generate generated results 380 including one or more estimated parameters of a second radiotherapy treatment plan optimization problem. The generated one or more estimated parameters of the second radiotherapy treatment plan optimization problem are then used by treatment processing logic 120 to solve the second optimization problem such as by using a simplex method, an interior point method, or sequential quadratic programming. The solution of the second optimization problem can then be directly used by treatment processing logic 120 to generate a radiotherapy treatment plan and/or decoded onto a space of the first optimization problem to estimate a solution to the first optimization problem.

Optimization problems typically possess two symmetry properties including equivariance to variable permutations and invariance to constraint permutations. Equivariance to variable permutations means that reordering the optimization variables gives a corresponding reordering of the solution (without affecting the optimal value of the objective function). Invariance to constraint permutations means that if the feasible set is described as a set of equalities and/or inequalities, then reordering them has no effect on the set of solutions (but could change the behavior of the optimization algorithm).

The class of permutation invariant functions may be characterized such that any permutation invariant function h(Y) operating on a set Y can be decomposed in the form according to Equation 9:

$$h(Y)=\rho(\Sigma_{y \in Y}\phi(y)) \qquad (9)$$

for some suitable transformations $\rho$ and $\phi$. This implies that a permutation invariant function can be learned by treatment processing logic 120 using this expression, e.g., by learning the transformations $\rho$ and $\phi$ with a ML algorithm such as a neural network. In some cases, permutation equivariant neural networks can be provided.

According to some embodiments, the mapping between parameters of the first optimization problem and the second optimization problem, G(u), may be defined by treatment processing logic 120 as a permutation invariant or equivariant neural network (ML model). Alternatively, the second optimization problem can be processed by treatment processing logic 120 based on permutation invariance or equivariance. If the result of processing the second optimization is permutation invariant, the parameters of the second optimization problem can be decoded by treatment processing logic 120 according to the original ordering of the parameters of the first optimization problem to invert the permutation. In this way, the decoded parameters recover the original ordering. It may be possible to limit the symmetry requirements just to some subset of the optimization variables or constraints (e.g., shots in the case of Gamma Knife planning).

To address size variability of the first optimization problem, the inputs can be processed with a fusion step that involves a quasi-arithmetic mean according to Equation 10:

$$\mu(\{y_1, \ldots, y_n\}) = \varphi^{-1}\left(\frac{1}{n}\sum_{k=1}^{n} \varphi(y_k)\right), \quad (10)$$

where ρ is an invertible function that could be specified a-priori or learned, e.g., using an invertible neural network. The quasi-arithmetic mean may also be permutation invariant. In another implementation, some parameters between the first and second optimization problems may be identified as being related through an underlying stochastic process. By the Kolmogorov extension theorem, any finite set of random variables from a stochastic process satisfies (i) exchangeability, which is essentially the same as permutation invariance; and (ii) consistency, which means that the random variables remaining after marginalizing out a subset still belong to the same stochastic process. Because of the consistency property, the optimization variables or parameters of the first optimization problem may be reduced by treatment processing logic 120 to a set of parameter variables with fixed size.

In some cases, the mapping function between the first and second optimization problems, G(u), is created by treatment processing logic 120 such that the second optimization problem has a fixed size and ordering relative to the first optimization problem. In such cases, the ML model (e.g., a neural network) is trained by treatment processing logic 120 to predict the solution of the second optimization problem. In this way, if G and $h_{dec}$ are differentiable, then any parameters could be trained in an end-to-end fashion.

In some embodiments, the original (first) optimization problem variables are encoded by treatment processing logic 120 to a lower dimensional representation $z = h_{enc}(x)$. In such implementations, the second optimization problem is defined by $g(z) = f(h_{dec}(z))$ and $Z = h_{enc}(X)$. In such cases, $G(u) = \{f \circ h_{dec}, h_{enc}(X)\}$, so that the solution to the second optimization problem is defined according to Equation 11:

$$z^* \in T[G(u)] = \underset{z \in h_{enc}(X)}{\arg\min} f(h_{dec}(z)). \quad (11)$$

The encoder and decoder could be different, and could be parameterized by treatment processing logic 120 using neural networks that could be trained to reconstruct the input, as explained above in connection with FIG. 3. In some implementations, a cycle-consistency constraint is used by treatment processing logic 120 in the training. In some embodiments, the decoder is the inverse of the encoder, and in such cases an invertible neural network can be used to learn the encoder and decoder.

In some embodiments, the first optimization problem is a quadratic programming problem. Such problems can be written in the general form by Equation 12:

$$\underset{x}{\text{minimize}}\; x^T Q_x x + p_x^T x \quad (12)$$
$$\text{subject to}\; A_x \leq 0$$

where $Q_x$ is a symmetric matrix (not necessarily positive definite), $p_x$ is a vector, and $A_x$ is a matrix. x* may be undefined a priori—it is determined by the optimization problem. An underlying stochastic process y(r) may be provided where the index variables r are known, such that $x = y(r_x)$. The stochastic process evaluated at $r_z$ is defined by $z = y(r_z)$. Selecting a z that is less complex than x allows the first optimization problem to be represented by the second optimization problem according to the stochastic process. y(r) may, for example, be a Gaussian process in which $y \sim GP(\mu(r), k(r; r'))$ where μ(r) is a mean function and k(r, r') is a covariance function. The Gaussian process assumption entails that $$\begin{pmatrix} x \\ z \end{pmatrix} \sim N\left(\begin{pmatrix} \mu_x \\ \mu_z \end{pmatrix}, \begin{pmatrix} k_{xx} & k_{xz} \\ k_{zx} & k_{zz} \end{pmatrix}\right) \quad (13)$$

where $\mu_x = \mu(r_x)$, $k_{xz} = k(r_x, r_z)$ etc. Given $z = y(r_z)$ at some chosen locations $r_z$, then such a condition can be used to estimate x, such as using Gaussian process regression. The conditional distribution is again Gaussian as shown in Equations 14-16:

$$x|z \sim N(\mu_{x|z}, \Sigma_{x|z}), \quad (14)$$

$$\mu_{x|z} = \mu_x + k_{xz} k_{zz}^{-1}(z - \mu_z), \quad (15)$$

$$\Sigma_{x|z} = k_{xx} - k_{xz} k_{zz}^{-1} k_{zx}. \quad (16)$$

This can be used to illustrate two different ways of formulating a second optimization problem (in z) based on the first optimization problem (in x). In the special case of quadratic programming where x and z are related through an underlying Gaussian process, these two approximations coincide. The first method for reformulating parameters of the first optimization problem by treatment processing logic 120 with parameters of a second optimization problem is to use a pointwise mapping, where x in the first optimization problem is replaced with the point estimate $\mu_{x|z}$. The second method consists of marginalizing all expressions in x over the conditional distribution by treatment processing logic 120.

In some implementations, parameters of the second optimization problem (in z) are reformulated by treatment processing logic 120 based on parameters of the first optimization problem (in x) based on the point estimate $\mu_{x|z}$. In such cases, by replacing the parameters (e.g., the optimization variables x) in the first optimization problem defined by Equation 12 with the point estimate $\mu_{z|z}$ from Equation 15 (ignoring the constant terms), the second optimization problem, which is also a quadratic optimization problem, is defined by Equation 17:

$$\underset{z}{\text{minimize}}\; z^T Q_z z + p_z^T z \quad (17)$$
$$\text{subject to}\; A_z z \leq \alpha$$

According to the second optimization problem, the optimization variables of the first optimization problems are defined by z and not x. In some cases, x can be represented by a fixed and much smaller set of points z. In some cases, z may be selected such that the matrices involved have some particular structure that is computationally advantageous over the parameters of the first optimization problem. In some implementations, rather than substituting z and x, an equality constraint can be used by treatment processing logic 120.

In some implementations, parameters of the second optimization problem (in z) are reformulated by treatment processing logic 120 based on parameters of the first optimization problem (in x) by marginalizing all expressions in x over the conditional distribution p(x|z). For simplicity, the convex case when $Q_x$ is positive definite is described, but the indefinite case could also be handled in a similar fashion. If $Q_x$ is positive definite, it has a Cholesky factorization $Q_x = L^T L$. From the general rules on linear transformations of normally distributed variables $s \sim N(\mu, \Sigma)$, it follows that $z = Ls$ is distributed according to Equation 18:

$$z \sim N(L\mu, L\Sigma L^T) \quad (18)$$

Also, from the definition of covariance, $E[ss^T] = \Sigma + \mu\mu^T$. Combining this expression with the covariance of z, the conditional expectation over the objective function is defined by Equations 19-23:

$$E[x^T Q_x x \mid z] = E[(Ly_{x|z})^T (Ly_{x|z})] \quad (19)$$

$$= E[Tr((Ly_{x|z})^T (Ly_{x|z}))] \quad (20)$$

$$= Tr(LE[y_{x|z}^T]L^T) \quad (21)$$

$$= Tr\left(L\Sigma_{x|z} L^T + L\mu_{x|z}\mu_{x|z}^T L^T\right) \quad (22)$$

$$= Tr(Q\Sigma_{x|z}) + \mu_{x|z}^T Q\mu_{x|z} \quad (23)$$

the first term, $Tr(Q\Sigma_{x|z})$, is a constant and thus irrelevant for the optimization. From Equation (18), it can be seen that $E[p_x^T x \mid z] = p_x^T \mu_{x|z}$, and $E[A_x x \mid z] = A_x \mu_{x|z}$. In conclusion, for a convex quadratic optimization problem, marginalization over the conditional distribution is equivalent to replacing x with the point estimate $\mu_{x|z}$. The resulting approximate second optimization problem is given in Equation 17. The indefinite case can be handled by using the eigenvalue decomposition and splitting the diagonal matrix into a positive and a negative part. By linearity, what results is a difference of two positive definite quadratic forms that can each be handled as above.

As one example, a scenario considering dose planning for Gamma Knife radiosurgery is described. A reasonably accurate model for the first optimization problem of the dose deposited by the Gamma Knife, at least some distance away from the surface, is defined according to Equation 24:

$$d(r) = \int \varphi(r-r')\rho(r')w(r')dr' = (\varphi * \rho w)(r), \quad (24)$$

where $\varphi(r, r')$ is the (translation invariant) dose rate kernel that gives the dose rate (for each of the 24 machine configurations) at position r from an isocenter at position r', i.e. $\varphi: \mathbb{R}^3 \times \mathbb{R}^3 \to \mathbb{R}^{24}$, $\rho(r')$ scales the dose rate by the density at r' and w(r') is the irradiation time of the 24 machine configurations at position r'. Current Gamma Knife treatments use a discrete set of isocenter locations $r_i$, $i=1, \ldots, n$, which means that $w(r') = \sum_{i=1}^{n} t_i \delta(r-r_i)$, where $\mathbb{R}^{24}$ is the irradiation times of the 24 configurations at position $r_i$.

According to the disclosed embodiments, the parameters of the first optimization problem (e.g., w) can be approximated by $w \sim GP(\mu(r'), k(r', r''))$, where the mean function $\mu(r)$ and covariance function $k(r, r')$ are appropriately parameterized functions. A useful property of the Gaussian process is that it's closed under linear functional transformations $L[w]$. In particular, the dose calculation in Equation 24 is such a transformation. Thus, the dose can be expressed by the second optimization problem described by a Gaussian process according to Equations 25-27:

$$d \sim GP(L[\mu], L^2[k]) \quad (25)$$

$$L[\mu] = (\varphi * \rho \mu)(r), \quad (26)$$

$$L^2[k] = \iint \rho(r')\varphi(r-r')k(r'-r'')\varphi(r-r'')^T \rho(r'')dr'dr''. \quad (27)$$

In this way, the first optimization problem can be approximated by the second optimization problem by treatment processing logic 120 by marginalization or point estimation.

In one example, the first optimization problem can be reformulated as a second optimization problem by treatment processing logic 120 by subsampling certain parameters of the first optimization problem. Specifically, considering a one-dimensional, dose planning problem where the delivered dose is a weighted combination of basis functions of the form defined by Equation 28:

$$\varphi(r,r') = \exp(-(r-r')^2) \quad (28)$$

This means that the delivered dose is $d(r) = \sum_{i=1}^{n} \varphi(r, r'_i) w_i = \Phi w$, where the n "isocenter locations" $r'_i$ are randomly chosen within the target and the prescribed dose is 1 inside the target and 0 outside. The goal is to determine the optimal setting of the nonnegative weights w. A reasonable way of formulating this optimization problem as the first optimization problem includes the nonnegative least-squares problem of Equation 29:

$$w^* = \underset{w \geq 0}{\operatorname{argmin}} \|\Phi w - \hat{d}\|_2. \quad (29)$$

The disclosed embodiments simplify the first optimization problem of Equation 29 using the second optimization problem defined by Equation 30 by subsampling the parameters w of the first optimization problem:

$$w_s^* = \underset{w_s \geq 0}{\operatorname{argmin}} \|\Phi w_s - \hat{d}\|_2. \quad (30)$$

Namely, the second optimization problem is defined by sampling a subset s of indices with corresponding weights $w_s$ and is solved only with respect to these (the others are effectively set to zero). In terms of the first optimization problem the corresponding (decoded) variables are $w = \{w_s$ if $i \in s$, 0 otherwise$\}$.

As another example of reducing the number of optimization variables, the first optimization problem according to Equation 31 is a smooth, constrained, non-convex problem:

$$\underset{x,y}{\operatorname{minimize}} \left(\frac{x}{a}\right)^2 + \left(\frac{y}{b}\right)^2 + \sin(2\pi(x\cos\beta + y\sin\beta)) \quad (31)$$

$$\text{subject to } x^2 + y^2 \geq R^2$$

$$y \geq 0$$

This form of optimization problem may arise many times with different values of the input parameters $u = \{a > 0, b > 0, \beta \in [0, \pi], R > 0\}$. The second optimization problem may be generated by the treatment processing logic 120 based on the input parameters u. For example, the treatment processing logic 120 may switch the first optimization problem decision variables to be expressed in polar coordinates to be solved only along a radial line, the angle of which is predicted by the ML model. In such circumstances, the original decision variables may be expressed in polar coordinates according to Equation 32:

$$x(r,\phi)=r\cos\phi,$$

$$y(r,\phi)=y\sin\phi. \quad (32)$$

The variable $\phi \in [0, \pi]$ may be predicted by the treatment processing logic 120 based on a trained ML model defined as $\phi = f_\theta(u)$ and held fixed during optimization.

Since the number and order of the input parameters is fixed in this example, a two-layer, fully connected, neural network (multilayer perceptron) can be used to predict $\phi$. Also, it follows from $\phi \in [0, \pi]$ and $r>0$ that the constraint $y>=0$ is automatically satisfied. Accordingly, the second optimization problem can be expressed by treatment processing logic 120 according to Equation 33 as a smooth, constrained, non-convex problem:

$$\underset{r}{\text{minimum}} \left(\frac{r\cos\phi}{a}\right)^2 + \left(\frac{r\sin\phi}{b}\right)^2 + \sin(2\pi(r\cos\phi\cos\beta + r\sin\phi\sin\beta)) \quad (33)$$

$$\text{subject to } r \geq R$$

As shown, the parameters x and y of the first optimization problem have been encoded into parameters $r\cos\phi$ and $r\sin\phi$ of the simpler second optimization problem using the trained ML model, where $\phi$ is predicted by the trained ML model.

Treatment processing logic 120 may solve the second optimization problem for a given set of input parameters u to obtain a solution $r^*=r^*(u)$, which, together with the predicted $\phi$, can be decoded into the decision variables of the first optimization problem using Equation 32.

In some embodiments, the parameters $\theta$ of the ML model $\phi = f_\theta(u)$ that predicts $\phi$ can be trained by the treatment processing logic 120 by encouraging the decoded solution to approximately solve the first optimization problem using the objective function of the first optimization problem as the loss function. Specifically, the loss function used to train the ML mode can be defined by Equation 34:

$$\ell(f_\theta(u)) = \left(\frac{r_* \cos f_\theta(u)}{a}\right)^2 + \left(\frac{r_* \sin f_\theta(u)}{a}\right)^2 + \quad (34)$$

$$\sin(2\pi(r*\cos f_\theta(u) \cdot \cos\beta + r*\sin f_\theta(u) \cdot \sin\beta))$$

This particular choice of loss function, which only makes use of the input parameters u and doesn't require knowledge of any solution, corresponds to the case of unsupervised training. The ML model may be applied to the first set of the training parameters to estimate a value for $\phi$. The estimated value of $\phi$ may be input to Equation 33 to provide the second optimization problem. Equation 33 is then solved using an optimization technique to obtain values for the parameters r of the second optimization problem. The obtained values of parameter r are input to Equation 34 (e.g., the solution to the second optimization problem using the estimated value of $\phi$) to compute a loss.

During supervised training, the parameter r of the second optimization problem is decoded according to Equation 32 onto a space of the first optimization problem (e.g., the parameter r is used to generate x and y parameter values). The decoded solution to the second optimization problem is compared to a batch of training solutions of the first optimization problem to compute a deviation. The batch of the training solutions of the first optimization problem can be used to train the ML model with the same parameters of the ML model and may range from one training solution to all of the training solutions. Training of the ML model is complete when a stopping criteria is met. In some embodiments, the stopping criteria comprises whether a maximum number of iterations has passed, if the loss is within a threshold amount or if the parameter updates are smaller than a threshold amount. If not, then parameters of the ML model are updated and used to generate another solution to the second optimization problem and corresponding solution to the first optimization problem based on another batch of training parameters of and solutions to the first optimization problem. Parameters of the ML model are updated and iterations of this training process continue for a specified number of iterations or epochs or until a given convergence or stopping criteria has been met.

During unsupervised training of the ML model is complete when a stopping criteria is met. In some embodiments, the stopping criteria comprises whether a maximum number of iterations has passed, if the loss is within a threshold amount or if the parameter updates are smaller than a threshold amount. If not, then parameters of the ML model are updated and used to generate another solution to the second optimization problem based on another batch of training parameters of the first optimization problem.

It is possible that the treatment processing logic 120 knows exactly what probability distributions the input parameters u follow, but it may not matter since training often minimizes empirical risk. Namely, the average value of the loss function of a fixed training dataset $\{u_i\}_{i=1}^n$ is expressed according to Equation 35:

$$\theta_* = \underset{\theta}{\text{argmin}} \sum_{i=1}^n \ell(f_\theta(u_i)). \quad (35)$$

As another example of mapping variable size problems to a fixed representation, a first optimization problem with different number and ordering of the decision variables can be mapped to a fixed size representation and expressed as a second optimization problem. This can be done by assuming that the decision variables belong to a stochastic process (e.g., a Gaussian Process). The first optimization problem can be phrased as a one-dimensional, dose planning problem where the delivered dose is a weighted combination of basis functions of the form expressed in Equation 36:

$$\varphi(r,r')=\exp(-(r-r')^2) \quad (36)$$

The input variables $u=\{r'_1, \ldots, r'_n\}$ is a set of variable size (e.g., n is not constant) corresponding to isocenter locations that are located inside a target tumor in a patient that extends from $r=-2$ to $r=2$. The delivered dose can be expressed according to Equation 37:

$$d(r, w) = \sum_{i=1}^n \varphi(r, r'_i) w_i = \Phi(r) w. \quad (37)$$

For simplicity, it can be assumed that the desired dose $\hat{d}$ is 1 inside the target tumor and 0 outside ($|r|>2$). The goal is to determine the optimal setting for the nonnegative weights w. Accordingly, the first optimization problem can be expressed as a nonnegative least-square problem as shown in Equation 38:

$$\underset{w}{\text{minimize}} \int_{-2}^{2} (d(r, w) - 1)^2 dr + \int_{|r|>2} d(r, w)^2 dr \quad (38)$$

subject $w \geq 0$

If the dose is evaluated on a grid, then the integrals become summations. For the sake of this example, the grid may be limited to $r \in \{-3, -2, -1, 0, 1, 2, 3\}$ resulting in the objective function of the first optimization problem to be expressed according to Equation 39:

$$\int_{-2}^{2}(d(r,w)-1)^2 dr + \int_{|r|>2} d(r,w)^2 dr = \quad (39)$$

$$\sum_{r=-2}^{2}(d(r,w)-1)^2 dr + d(-3,w)^2 + d(3,w)^2 ==$$

$$\sum_{r=-3}^{3}(\Phi(r)w - \hat{d}(r))^2 == w^t \Phi^t \Phi w - 2\hat{d}^t \Phi w + \hat{d}^{t'} \hat{d},$$

where the last expression assumes an implicit summation over r. Accordingly, the first optimization problem can be rewritten as the quadratic optimization problem according to Equation 40:

$$\underset{w}{\text{minimize}} \; w^t \Phi^t \Phi w - 2\hat{d}^t \Phi w \quad (40)$$

subject to $w \geq 0$

In some embodiments, the first optimization problem defined by Equation 40 can be simplified to a second optimization problem by sampling a subset s of indices with corresponding weights $w_s$. The second optimization problem can then be solved only according to these sampled values where the remaining are 0. In this way, the decoded variables of the first optimization problem can be expressed as $w = \{w_s \text{ if } i \in s, 0 \text{ otherwise}\}$.

In some embodiments, rather than sampling, according to some embodiments, the second optimization problem can be defined by applying a Gaussian Process model to the weights. Specifically, a number of synthetic isocenter locations $u^*$ can be used that may or may not include elements of the observed isocenter locations. These synthetic isocenter locations can be selected according to some heuristic or by training based on a set of observed problem instances. In some implementations, the isocenter locations can be defined as $u^* = \{-2, 0, 2\}$. Assuming that the weights can be modelled as random samples from a Gaussian Process, with zero mean and a covariance function given by the spatial proximity according to an Exponential kernel, the following Equations 41 and 42 can be expressed:

$$\mu(r) = 0, \quad (41)$$

$$k(r, r') = \exp\left(-\frac{|r-r'|}{\Delta}\right) \quad (42)$$

where $\Delta$ is a hyperparameter (the lengthscale of correlations) that may be selected based on some heuristic or training. Equations 41 and 42 can be used as the functions that map parameters or variables of the first optimization problem to the parameters and variables of the second optimization problem.

The optimization variables of the first optimization problem are $x = \{w_{-1}, w_0, w_1, w_2\}$ while the optimization variables of the second optimization problem are $z = \{w_{-2}, w_0, w_2\}$. The treatment processing logic 120 can reformulate the first optimization problem as the second optimization problem in z by replacing x in the first optimization problem by a point estimate based on z and optimizing with respect to z instead of x using Equations 41 and 42. The conditional mean of the Gaussian Process can be used as the point estimate according to Equation 43:

$$x(z) = k(u_1, u_*)k(u_*u_*)^{-1}z == \begin{pmatrix} k(-1,-2) & k(-1,0) & k(-1,2) \\ k(0,-2) & k(0,0) & k(0,2) \\ k(1,2) & k(1,0) & k(1,2) \\ k(2,-2) & k(2,0) & k(2,2) \end{pmatrix} \quad (43)$$

$$\begin{pmatrix} k(-2,-2) & k(-2,0) & K(0=-2,2) \\ k(0,-2) & k(0,0) & k(0,2) \\ k(2,-2) & k(2,0) & k(2,2) \end{pmatrix}^{-1} z$$

To clean up the notation, $\tilde{\Phi} = \Phi k(u_1, u^*)k(u^*,u^*)^{-1}$ can be introduced to rephrase the second optimization problem according to Equation 44:

$$\underset{z}{\text{minimize}} \; z^t \tilde{\Phi}^t \tilde{\Phi} z - 2\hat{d}^t \tilde{\Phi} z \quad (44)$$

subject to $k(u_1, u_*)k(u_*, u_*)^{-1} z \geq 0$.

Figure 4:
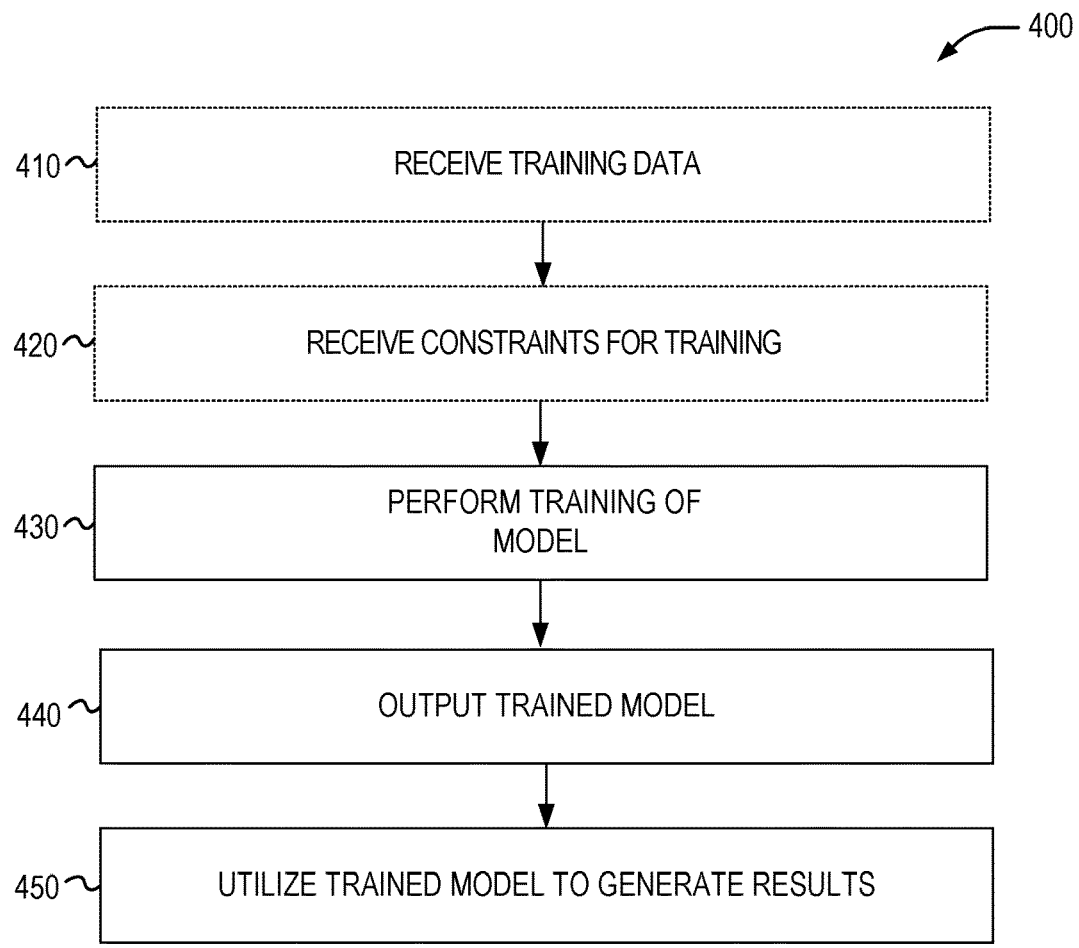
FIGS. 4-6 illustrate flowcharts of exemplary operations for training and using a machine learning technique to estimate parameters of a second radiotherapy treatment plan optimization problem from parameters of a first radiotherapy treatment plan optimization problem, according to some examples of the disclosure.

FIG. 4 is a flowchart illustrating example operations of the treatment processing logic 120 in performing a process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 receives training data. For example, treatment processing logic 120 receives pairs of one or more training optimization variables and training parameters of a plurality of training radiotherapy treatment plan optimization problems; pairs of one or more training optimization variables and training parameters of a plurality of training radiotherapy treatment plan optimization problems and solutions to the plurality of training radiotherapy treatment optimization problems; and pairs of one or more training optimization variables and training parameters of a plurality of training radiotherapy treatment plan optimization problems of a given type.

At operation 420, treatment processing logic 120 receives constraints for training.

At operation 430, treatment processing logic 120 performs training of the model. For example, treatment processing logic 120 may train the ML model parameters 312 (FIG. 3) by minimizing a loss function based on one or more solutions to a first batch of first radiotherapy treatment plan optimization problems and the corresponding training parameters of the first batch of first radiotherapy treatment plan optimization problems. In this way, the ML model is trained to establish a relationship between parameters of a second radiotherapy treatment plan optimization problem and parameters of the plurality of the first training radiotherapy treatment plan optimization problems. The training can be performed in a supervised or unsupervised manner.

At operation 440, treatment processing logic 120 outputs the trained model. For example, the trained model can be output and stored in a memory or parameters of the model can be presented on a display device to a clinician.

At operation 450, treatment processing logic 120 utilizes the trained model to generate results. For example, after each of the machine learning models $\hat{A}_\Theta$ (sometimes referred to as $\Lambda_\Theta$) is trained, new data 370, including one or more patient input parameters of a first radiotherapy treatment plan optimization problem, may be received. The trained machine learning technique $\hat{A}_\Theta$ may be applied to the new data 370 to generate generated results 380 including one or more parameters of a second optimization problem.

Figure 5:
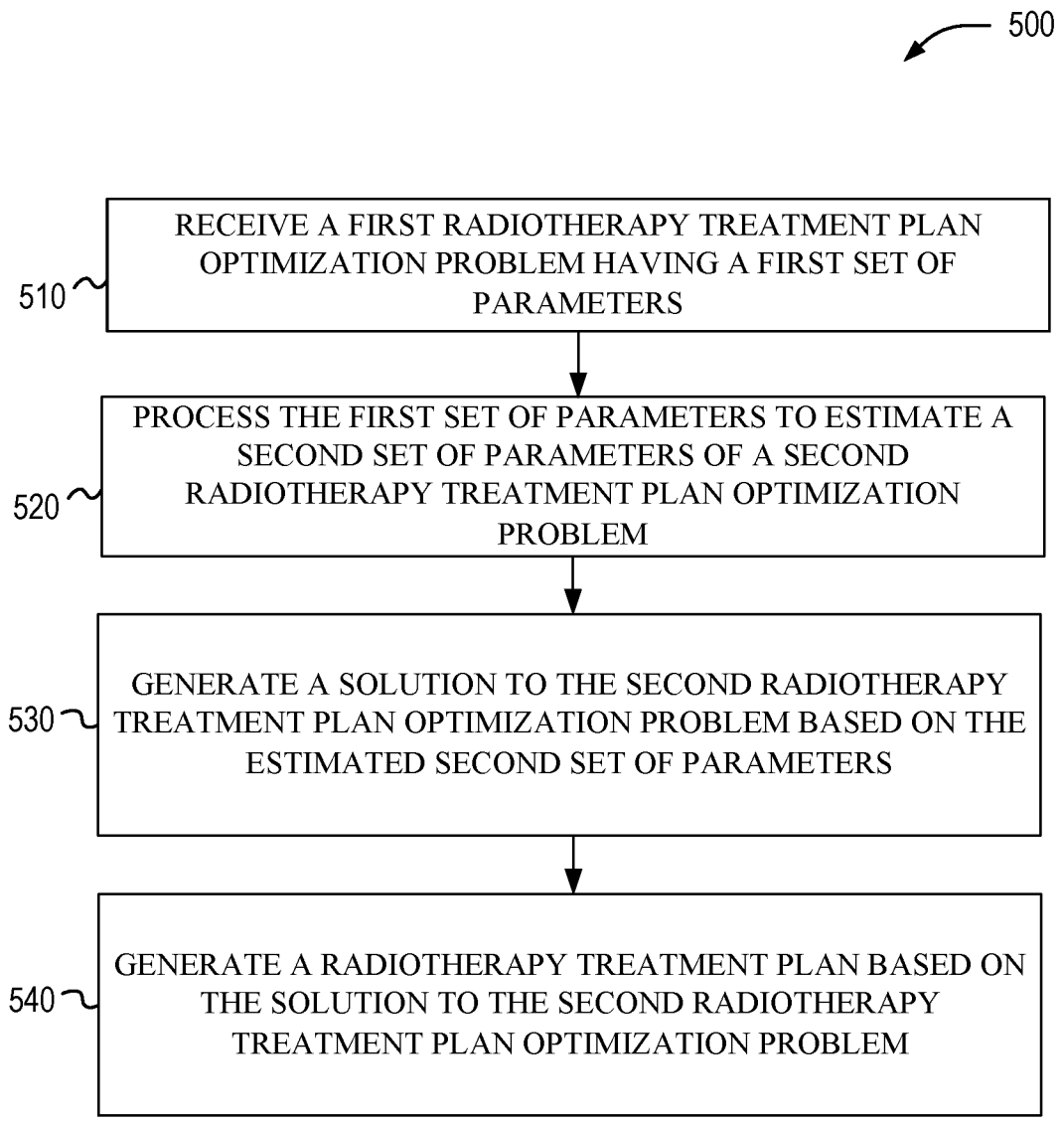

FIG. 5 is a flowchart illustrating example operations of the treatment processing logic 120 in performing a process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 510, treatment processing logic 120 receives a first radiotherapy treatment plan optimization problem having a first set of parameters.

At operation 520, treatment processing logic 120 processes the first set of parameters to estimate a second set of parameters of a second radiotherapy treatment plan optimization problem.

At operation 530, treatment processing logic 120 generates a solution to the second radiotherapy treatment plan optimization problem based on the estimated second set of parameters.

At operation 540, treatment processing logic 120 generates a radiotherapy treatment plan based on the solution to the second radiotherapy treatment plan optimization problem.

Figure 6:
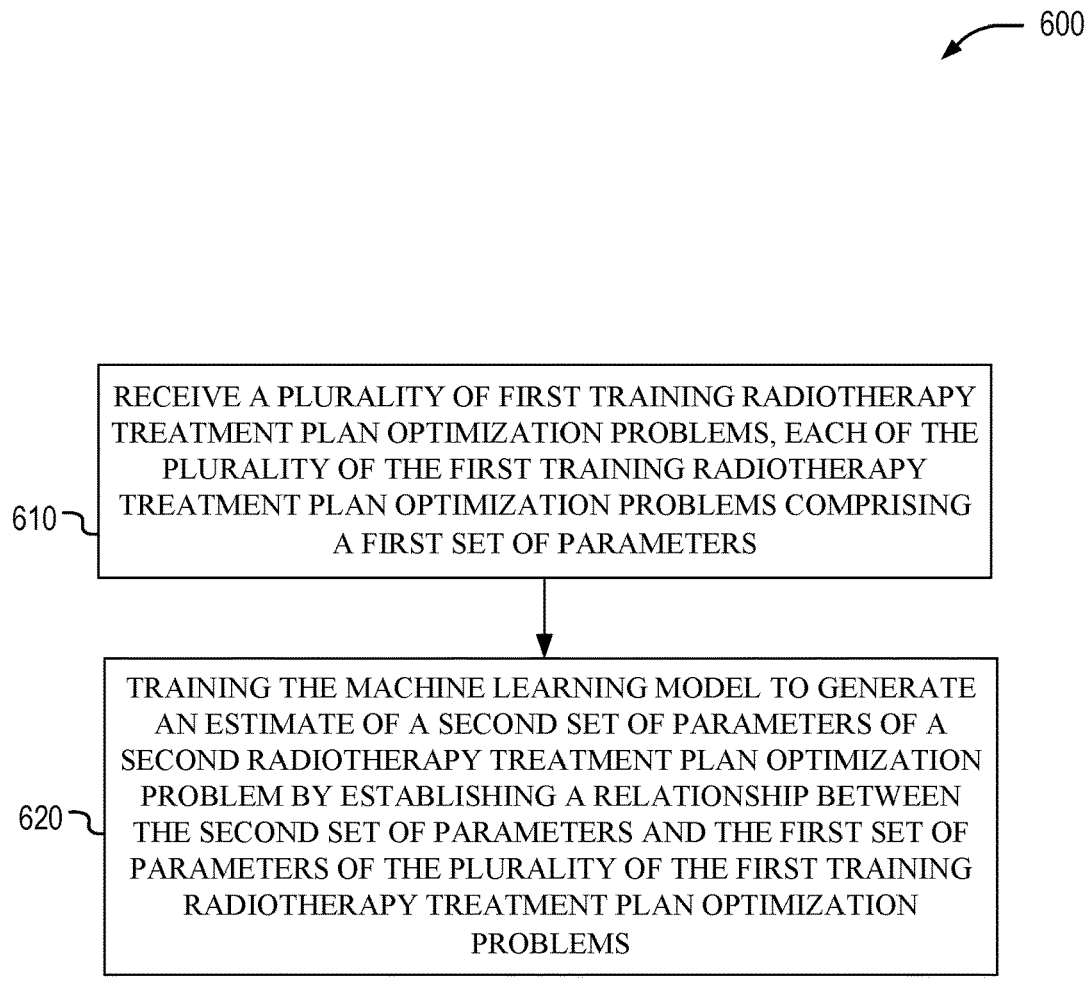

FIG. 6 is a flowchart illustrating example operations of the treatment processing logic 120 in performing a process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 610, treatment processing logic 120 receives a plurality of first training radiotherapy treatment plan optimization problems, each of the plurality of the first training radiotherapy treatment plan optimization problems comprising a first set of parameters.

At operation 620, treatment processing logic 120 trains the machine learning model to generate an estimate of a second set of parameters of a second radiotherapy treatment plan optimization problem by establishing a relationship between the second set of parameters and the first set of parameters of the plurality of the first training radiotherapy treatment plan optimization problems.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the training or prediction operations from FIG. 3, operate the trained treatment model 360, perform or implement the operations of the flowcharts for processes 400-600, or perform any one or more of the other methodologies discussed herein (e.g., as part of treatment processing logic 120). In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matters contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials, and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for solving a radiotherapy treatment plan optimization problem, the method comprising:
receiving, by processor circuitry, a first radiotherapy treatment plan optimization problem having a first set of parameters, the first set of parameters of the first radiotherapy treatment plan optimization problem comprising a first objective function, a first set of optimization variables, and a first set of constraints;

converting the first radiotherapy treatment plan optimization problem into a second radiotherapy treatment plan optimization problem having a second set of parameters, the second set of parameters comprising the first objective function, a second set of optimization variables, and the first set of constraints, the second set of optimization variables being determined by processing the first set of optimization variables of the first radiotherapy treatment plan optimization problem, the converting comprising:
  training a first machine learning model to encode one or more variables of the first radiotherapy treatment plan optimization problem into a lower dimensional representation;
  processing, by the processor circuitry, the lower dimensional representation encoded by the first machine learning model as the second set of parameters of the second radiotherapy treatment plan optimization problem;
  applying an optimization process to generate, by the processor circuitry, a solution to the second radiotherapy treatment plan optimization problem based on the second set of parameters;
  training, jointly with the first machine learning model, a second machine learning model to generate an output that decodes the parameters of the second radiotherapy treatment plan optimization problem back to the first set of parameters of the first radiotherapy treatment plan optimization problem; and
  mapping the solution to the second radiotherapy treatment plan optimization problem to a space of the first radiotherapy treatment plan optimization problem using the output of the second machine learning model to generate a decoded solution of the second radiotherapy treatment plan optimization problem; and
solving the first radiotherapy treatment plan optimization problem using the decoded solution of the second radiotherapy treatment plan optimization problem to generate a radiotherapy treatment plan.

2. The method of claim 1, wherein converting comprises replacing the first set of optimization variables with a point estimate to generate the second radiotherapy treatment plan optimization problem having the second set of parameters, wherein the second set of parameters are selected from a class of optimization problems associated with a different solver than a solver of the first radiotherapy treatment plan optimization problem.

3. The method of claim 1, further comprising converting the first radiotherapy treatment plan optimization problem from being a non-convex optimization problem to being a convex optimization problem comprising the second radiotherapy treatment plan optimization problem, wherein the second machine learning model is trained to decode the second set of parameters of the second radiotherapy treatment plan optimization problem according to an original ordering of the first set of parameters in the first radiotherapy treatment plan optimization problem to invert a permutation of the second set of parameters.

4. The method of claim 1, wherein a first optimization variable in the first set of parameters is excluded from the second set of parameters, and wherein the first radiotherapy treatment plan optimization problem is non-convex and the second radiotherapy treatment plan optimization problem is convex.

5. The method of claim 1, wherein the converting the first radiotherapy treatment plan optimization problem from being a general nonlinear problem to a semidefinite programming problem comprising the second radiotherapy treatment plan optimization problem.

6. The method of claim 1, wherein processing the first set of parameters comprises applying at least one of a non-linear functional relationship or a statistical model to the first set of parameters, wherein the statistical model comprises modeling the first set of parameters as random variables dependent on the second set of parameters and an objective function or constraint of the second radiotherapy treatment plan optimization problem is derived based on a measure of central tendency of the objective function or constraint of the first radiotherapy treatment plan optimization problem.

7. The method of claim 1, wherein the second radiotherapy treatment plan optimization problem includes fewer constraints than the first radiotherapy treatment plan optimization problem, and wherein the first radiotherapy treatment plan optimization problem is solved by quadratic programming and the second radiotherapy treatment plan optimization problem is solved by linear programming.

8. The method of claim 1, wherein a same batch of training data is used to train both the first and second machine learning models, wherein a matrix in the second radiotherapy treatment plan optimization problem is sparse or structured in correspondence with a matrix in the first radiotherapy treatment plan optimization problem, and wherein generating the solution comprises processing the second radiotherapy treatment plan optimization problem using an optimization process.

9. The method of claim 1, wherein the solution to the second radiotherapy treatment plan optimization problem is invariant or equivariant to permutations of first and second subsets of the first set of parameters, further comprising solving the second radiotherapy treatment plan optimization problem to find at least one point that is within a specified tolerance to a solution to the first radiotherapy treatment plan optimization problem.

10. The method of claim 9, wherein the second radiotherapy treatment plan optimization problem has a fixed size relative to a size of the first radiotherapy treatment plan optimization problem, further comprising:
  training the first and second machine learning models to establish a relationship between the first set of parameters of the first radiotherapy treatment plan optimization problem and the second set of parameters of the second radiotherapy treatment plan optimization problem; and
  decoding, based on the established relationship, a solution to the second radiotherapy treatment plan optimization problem to generate an approximate solution to the first radiotherapy treatment plan optimization problem, the approximate solution being used to solve the first radiotherapy treatment plan optimization problem.

11. The method of claim 1, further comprising:
  expressing the first set of parameters comprising decision variables in polar coordinates to be solved only along a radial line; and
  applying the first machine learning model to the first set of parameters to predict a particular angle along which to solve the decision variables in the polar coordinates only along the radial line, wherein the second machine learning model decodes the second set of parameters of the second radiotherapy treatment plan optimization problem back to the first set of parameters of the first radiotherapy treatment plan optimization problem based on the particular angle predicted by the first machine learning model.

12. The method of claim 1, wherein the first radiotherapy treatment plan optimization problem comprises at least one of a linear programming problem or a quadratic programming problem, and wherein the first and second sets of parameters are related through a Gaussian process.

13. The method of claim 12 further comprising:
computing a second parameter of the second set of parameters based on a point estimate corresponding to a Gaussian distribution of a first parameter in the first set of parameters; and
replacing the first parameter in the first set of parameters with the second parameter to generate the second radiotherapy treatment plan optimization problem, wherein the second radiotherapy treatment plan optimization problem comprises another linear or quadratic programming problem.

14. The method of claim 1 further comprising marginalizing the first set of parameters over a Gaussian distribution to estimate the second set of parameters.

15. The method of claim 1, wherein the second machine learning model corresponds to an inverse of the first machine learning model and each comprises an invertible neural network.

16. The method of claim 1, applying a third machine learning model to the solution to estimate another solution to the first radiotherapy treatment plan optimization problem.

17. The method of claim 1, wherein the first and second radiotherapy treatment plan optimization problems are processed by an optimization process until a predetermined criterion is met.

18. A method for training a machine learning model to solve a radiotherapy treatment plan optimization problem, the method comprising:
receiving, by processor circuitry, a plurality of first training radiotherapy treatment plan optimization problems, each of the plurality of the first training radiotherapy treatment plan optimization problems comprising a first set of parameters, the first set of parameters of the first training radiotherapy treatment plan optimization problems comprising a first objective function, a first set of optimization variables, and a first set of constraints; and
converting the first training radiotherapy treatment plan optimization problems into one or more second radiotherapy treatment plan optimization problems having a second set of parameters, the second set of parameters comprising the first objective function, a second set of optimization variables, and the first set of constraints, the second set of optimization variables being determined by processing the first set of optimization variables, the converting comprising:
training a first machine learning model to encode one or more variables of the first radiotherapy treatment plan optimization problem into a lower dimensional representation to estimate the second set of parameters of the second radiotherapy treatment plan optimization problem by establishing a relationship between the second set of parameters and the first set of parameters of the plurality of the first training radiotherapy treatment plan optimization problems;
training, jointly with the first machine learning model, a second machine learning model to generate an output that decodes the parameters of the second radiotherapy treatment plan optimization problem back to the first set of parameters of the first radiotherapy treatment plan optimization problem;
mapping a solution to the second radiotherapy treatment plan optimization problem to a space of the first radiotherapy treatment plan optimization problem using the output of the second machine learning model to generate a decoded solution of the second radiotherapy treatment plan optimization problem; and
solving the first radiotherapy treatment plan optimization problem using the decoded solution of the second radiotherapy treatment plan optimization problem to generate a radiotherapy treatment plan.

19. The method of claim 18, wherein the first machine learning model is trained in a supervised approach by:
obtaining a first training data pair comprising a given one of the first set of parameters and a corresponding solution to a given one of the plurality of first training radiotherapy treatment plan optimization problems;
processing the given one of the first set of parameters with the machine learning model to generate the estimate of the second set of parameters of the second radiotherapy treatment plan optimization problem;
solving the second radiotherapy treatment plan optimization problem based on the estimate of the second set of parameters to generate a given solution to the second radiotherapy treatment plan optimization problem;
comparing the given solution and the corresponding solution; and
updating first machine learning model based on the comparing.

20. The method of claim 18, wherein the first machine learning model is trained in an unsupervised approach by:
obtaining a given one of the first set of parameters;
processing the given one of the first set of parameters with the machine learning model to generate the estimate of the second set of parameters of the second radiotherapy treatment plan optimization problem;
solving the second radiotherapy treatment plan optimization problem based on the estimate of the second set of parameters to generate a given solution to the second radiotherapy treatment plan optimization problem;
evaluating the given solution against a metric; and
updating the first machine learning model based on the evaluation of the given solution.

21. The method of claim 20, wherein the metric comprises a statistical metric representing a likelihood of observing training data or a utility of a treatment plan corresponding to the given solution.

22. A non-transitory computer-readable medium comprising non-transitory computer-readable instructions, the computer-readable instructions comprising instructions for performing operations comprising:
receiving a first radiotherapy treatment plan optimization problem having a first set of parameters, the first set of parameters of the first radiotherapy treatment plan optimization problem comprising a first objective function, a first set of optimization variables, and a first set of constraints;
converting the first radiotherapy treatment plan optimization problem into a second radiotherapy treatment plan optimization problem having a second set of parameters, the second set of parameters comprising the first objective function, a second set of optimization variables, and the first set of constraints, the second set of optimization variables being determined by processing the first set of optimization variables of the first radiotherapy treatment plan optimization problem, the converting comprising:

training a first machine learning model to encode one or more variables of the first radiotherapy treatment plan optimization problem into a lower dimensional representation;

processing the lower dimensional representation encoded by the first machine learning model as the second set of parameters of the second radiotherapy treatment plan optimization problem;

applying an optimization process to generate a solution to the second radiotherapy treatment plan optimization problem based on the second set of parameters; and training, jointly with the first machine learning model, a second machine learning model to generate an output that decodes the parameters of the second radiotherapy treatment plan optimization problem back to the first set of parameters of the first radiotherapy treatment plan optimization problem; and mapping the solution to the second radiotherapy treatment plan optimization problem to a space of the first radiotherapy treatment plan optimization problem using the output of the second machine learning model to generate a decoded solution of the second radiotherapy treatment plan optimization problem; and solving the first radiotherapy treatment plan optimization problem using the decoded solution of the second radiotherapy treatment plan optimization problem to generate a radiotherapy treatment plan.

23. The non-transitory computer-readable medium of claim 22, wherein the second set of parameters are selected from a class of optimization problems associated with a different solver than a solver of the first radiotherapy treatment plan optimization problem.

24. A system comprising:
a memory for storing instructions; and
one or more processors for executing the instructions stored in the memory for performing operations comprising:
receiving a first radiotherapy treatment plan optimization problem having a first set of parameters, the first set of parameters of the first radiotherapy treatment plan optimization problem comprising a first objective function, a first set of optimization variables, and a first set of constraints;

converting the first radiotherapy treatment plan optimization problem into a second radiotherapy treatment plan optimization problem having a second set of parameters, the second set of parameters comprising the first objective function, a second set of optimization variables, and the first set of constraints, the second set of optimization variables being determined by processing the first set of optimization variables of the first radiotherapy treatment plan optimization problem, the converting comprising:

training a first machine learning model to encode one or more variables of the first radiotherapy treatment plan optimization problem into a lower dimensional representation;

processing the lower dimensional representation encoded by the first machine learning model as the second set of parameters of the second radiotherapy treatment plan optimization problem;

applying an optimization process to generate a solution to the second radiotherapy treatment plan optimization problem based on the second set of parameters;

training, jointly with the first machine learning model, a second machine learning model to generate an output that decodes the parameters of the second radiotherapy treatment plan optimization problem back to the first set of parameters of the first radiotherapy treatment plan optimization problem; and mapping the solution to the second radiotherapy treatment plan optimization problem to a space of the first radiotherapy treatment plan optimization problem using the output of the second machine learning model to generate a decoded solution of the second radiotherapy treatment plan optimization problem; and solving the first radiotherapy treatment plan optimization problem using the decoded solution of the second radiotherapy treatment plan optimization problem to generate a radiotherapy treatment plan.

25. The system of claim 24, wherein the second set of parameters are selected from a class of optimization problems associated with a different solver than a solver of the first radiotherapy treatment plan optimization problem.

* * * * *